US006812352B2

(12) United States Patent
Kreutzer et al.

(10) Patent No.: US 6,812,352 B2
(45) Date of Patent: Nov. 2, 2004

(54) MULTIDENTATE PHOSPHITE LIGANDS, CATALYTIC COMPOSITIONS CONTAINING SUCH LIGANDS, AND CATALYTIC PROCESSES UTILIZING SUCH CATALYTIC COMPOSITIONS

(75) Inventors: Kristina Ann Kreutzer, Wilmington, DE (US); Wilson Tam, Boothwyn, PA (US); J. Michael Garner, Wilmington, DE (US); John Ronald Boyles, Wilmington, DE (US)

(73) Assignee: Invista North America S.a.r.l., Wichita, KS (US)

( * ) Notice: Subject to any disclaimer, the term of this patent is extended or adjusted under 35 U.S.C. 154(b) by 0 days.

(21) Appl. No.: 10/118,551

(22) Filed: Apr. 9, 2002

(65) Prior Publication Data

US 2003/0023110 A1 Jan. 30, 2003

Related U.S. Application Data

(63) Continuation of application No. 09/650,583, filed on Aug. 30, 2000, now abandoned.
(60) Provisional application No. 60/154,727, filed on Sep. 20, 1999.

(51) Int. Cl.$^7$ .................. C07C 253/10; C07D 319/06; C07D 315/00; C07D 307/02
(52) U.S. Cl. ................... 549/373; 549/374; 549/426; 549/427; 549/428; 549/452; 549/491; 558/338
(58) Field of Search .................. 558/338; 502/162; 549/373, 374, 426, 427, 428, 452, 491

(56) References Cited

U.S. PATENT DOCUMENTS

| 3,496,215 A | 2/1970 | Drinkard et al. |
| 3,496,217 A | 2/1970 | Drinkard, Jr. et al. |
| 3,536,748 A | 10/1970 | Drinkard, Jr. et al. |
| 3,676,481 A | 7/1972 | Chia |
| 3,907,847 A | 9/1975 | Keblys |
| 5,210,260 A | 5/1993 | Bohshar et al. |
| 5,235,113 A | 8/1993 | Sato et al. |
| 5,512,696 A | 4/1996 | Kreutzer et al. ............. 558/338 |
| 5,663,369 A | 9/1997 | Kreutzer et al. ............. 549/212 |
| 5,688,986 A | 11/1997 | Tam et al. .................. 558/338 |
| 5,723,641 A | 3/1998 | Tam et al. .................... 556/13 |
| 5,821,378 A | 10/1998 | Foo et al. .................... 558/338 |
| 5,847,191 A | 12/1998 | Bunel et al. ................. 558/338 |
| 5,910,600 A | 6/1999 | Urata et al. ................. 558/162 |

FOREIGN PATENT DOCUMENTS

| DE | 19717359 | 11/1997 | |
| WO | WO 95/14659 | 6/1995 | |
| WO | WO 95/30680 | 11/1995 | |
| WO | WO 96/16022 | 5/1996 | |
| WO | WO 96/22968 | 8/1996 | |
| WO | WO 99/06357 | 2/1999 | ......... C07C/253/10 |
| WO | WO 99/06359 | 2/1999 | |

OTHER PUBLICATIONS

Donald L. Jameson, et al., Design and Synthesis of a Series of Facially Coordinating Tridentate Ligands, Tetrahedron Letters (1989) pp. 1609–1612, vol. 30, No. 13, Gettysburg, PA.

Gregory D. Cuny, et al., Practical, High–Yield Regloselective, Rhodium–Catalyzed Hydroformylation of Functionalized a–Olefins, J.A. Chem. Soc. (1993) pp. 2066–2068, vol. 115.

Leonard E. Miller, et al., The Reactivity of the Methyl Group In 2–Methyl–3–nhronaphthalene, J. A. Chem. Soc. (1954) pp. 296–297, vol. 76.

Giovanni Casiraghi, et al., Uncatalyzed Phenol–Formaldehyde Reactions. A Convenient Synthesis of Substituted 2,2'Dihydroxy–diphanylmethanes, Synthesis (1981) pp. 143–146, vol. 2.

Warren W Kaeding Oxidation of Phenols with Cupric Salts, Journal of Organic Chemistry, (1983). Pp. 1063–1067, vol. 28.

T. Jongsma P. Kimes, et al., A New Type of Highly Active Polymer–Bound Rhodium Hydroformylation Catalyst, Polymer (1992) pp. 161–165, vol. 33.

Wei–Bo Wang, et al., An Efficient SbClS–Metal System for Allylation, Reduction and Acetalization of Aldehydes, Tetrahedron (1990) pp. 3315–3320, vol. 46, No. 9.

Martin Hovorka, et al., Highly Selective Oxidative Cross–Coupling of Substituted 2–Naphthols: A Convenient Approach to Unsymmetrical 1, 1–Bimaphthalene–2, 2'–Diols. Tetrahedron Letters (1990) pp. 413–416, vol. 31, No. 3.

B.F. Gisin, The Preparation of Merrifield–Resins Through Total Esterification With Ceslum Salts, Helvetica Chimica Acta 1973) pp. 1476–1482, vol. 58, Fasc. 5.

Claire Le, Hetet, Synthesis of Functionalized γ and o–Lactones via Polymer–Bound Epoxides. Tetrahedron Letters (1997) pp. 5153–5156, vol. 38, No. 29.

Achim Kless, The First Chiral Early–Late Heterobimetallic Complex–A Titanium(IV)–Palladium(II) Complex Based on Selenophos, Tetrahedron (1996) pp. 14599–14606, vol. 52, No. 46.

Anderson De Farias Dias, An Improved High Yield Synthesis of Dehydrodieugenol, Phytochemistry (1988) pp. 3008–3009, vol. 27, No. 9.

(List continued on next page.)

Primary Examiner—Ceila Chang
Assistant Examiner—Ebenezer Sackey
(74) Attorney, Agent, or Firm—John A. Langworthy

(57) ABSTRACT

Multidentate phosphite ligands are disclosed for use in reactions such as hydrocyanation and isomerization. The catalyst compositions made therefrom and the various catalytic processes which employ such multidentate phosphite ligands are also disclosed. In particular, the ligands have heteroatom-containing substituents on the carbon attached to the ortho position of the terminal phenol group.

9 Claims, No Drawings-

OTHER PUBLICATIONS

Martin Hovorka, et al. An Optimized Synthesis of Dimethyl 2,2'–Dihydroxy–1,1'–Binaphthalene–3,3'–Dicarboxylate and Methyl 2 2'–Dihydroxy–1,1'–Binaphthalane–3–Carboxylate, Organic Prep. and Proc. International (1991) pp. 200–203, vol. 23, No. 2.

John T. Pinhey, et al. The Thermal ortho–Substitution, Aust. J. Chem. (1988) pp. 69–80, vol. 41.

Fukiko Yamada, et al., Substituted Bisphenois as Antioxidants for Autoxidation of Tetrain, The Chemical Society of Japan—Bull. Chem. Soc. (1989) pp. 3603–3608, vol. 62.

Baker et al, Chelating Diphosphite Complexes of Nickel (0) and Platinum (0): Their Remarkable Stability and Hydrocyanation Activity, J. Chem. Soc., Chem. Commun., 803–804, 1991.

MULTIDENTATE PHOSPHITE LIGANDS, CATALYTIC COMPOSITIONS CONTAINING SUCH LIGANDS, AND CATALYTIC PROCESSES UTILIZING SUCH CATALYTIC COMPOSITIONS

CROSS REFERENCE TO RELATED APPLICATION

This application is a continuation of U.S. application Ser. No. 09/650,583, filed Aug. 30, 2000, now abn. which is incorporated in its entirety herein, which claimed the benefit of U.S. Provisional Application No. 60/154,727 filed 20 Sep. 1999.

FIELD OF THE INVENTION

The invention relates to certain multidentate phosphite ligands, the catalyst compositions made therefrom and catalytic processes which employ such multidentate phosphite ligands. In particular, the ligands have heteroatom-containing substituents on the carbon attached to the ortho position of the terminal phenol group. The catalytic processes exemplified herein are hydrocyanation and isomerization.

TECHNICAL BACKGROUND OF THE INVENTION

Phosphorus ligands are ubiquitous in catalysis and are used for a number of commercially important chemical transformations. Phosphorus ligands commonly encountered in catalysis include phosphines (A), and phosphites (B), shown below. In these representations, R can be virtually any organic group. Monophosphine and monophosphite ligands are compounds which contain a single phosphorus atom which serves as a donor to a metal. Bisphosphine, bisphosphite, and bis(phosphorus) ligands in general, contain two phosphorus donor atoms and normally form cyclic chelate structures with transition metals.

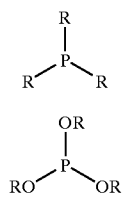

There are several industrially important catalytic processes employing phosphorus ligands. For example, U.S. Pat. No. 5,910,600 to Urata, et al. discloses that bisphosphite compounds can be used as a constituting element of a homogeneous metal catalyst for various reactions such as hydrogenation, hydroformylation, hydrocyanation, hydrocarboxylation, hydroamidation, hydroesterification and aldol condensation.

Some of these catalytic processes are used in the commercial production of polymers, solvents, plasticizers and other commodity chemicals. Consequently, due to the extremely large worldwide chemical commodity market, even small incremental advances in yield or selectivity in any of these commercially important reactions are highly desirable. Furthermore, the discovery of certain ligands that may be useful for applications across a range of these commercially important reactions is also highly desirable not only for the commercial benefit, but also to enable consolidation and focusing of research and development efforts to a particular group of compounds.

U.S. Pat. No. 5,512,696 to Kreutzer, et al. discloses a hydrocyanation process using a multidentate phosphite ligand, and the patents and publications referenced therein describe hydrocyanation catalyst systems pertaining to the hydrocyanation of thylenically unsaturated compounds. U.S. Pat. Nos. 5,723,641, 5,663,369, 5,688,986 and 5,847,191 disclose processes and catalyst compositions for the hydrocyanation of monoethylenically unsaturated compounds using zero-valent nickel and multidentate phosphite ligands, and Lewis acid promoters.

U.S. Pat. No. 5,821,378 to Foo, et al. discloses a liquid phase process for the hydrocyanation of diolefinic compounds to produce nonconjugated acyclic nitriles as well as a liquid phase process for the isomerization of those nitriles to 3- and/or 4-monoalkene linear nitrites where the reactions are carried out in the presence of zero-valent nickel and a multidentate phosphite ligand. Other catalytic processes for the hydrocyanation of olefins and the isomerization of monoalkene nitrites are described in the patents and publications referenced therein. Commonly assigned, published PCT Application WO99/06357 discloses multidentate phosphite ligands having alkyl ether substituents on the carbon attached to the ortho position of the terminal phenol group for use in a liquid phase process for the hydrocyanation of diolefinic compounds to produce nonconjugated acyclic nitrites as well as a liquid phase process for the isomerization of those nitrites to 3- and/or 4monoalkene linear nitrites.

While the catalyst systems described above may represent commercially viable catalysts, it always remains desirable to provide even more effective, higher performing catalyst precursor compositions, catalytic compositions and catalytic processes to achieve full commercial potential for a desired reaction. The effectiveness and/or performance may be achieved in any or all of rapidity, selectivity, efficiency or stability, depending on the reaction performed. It is also desirable to provide such improved catalyst systems and/or processes which may be optimized for one or more commercially important reactions such as hydroformylation, hydrocyanation or isomerization. Other objects and advantages of the present invention will become apparent to those skilled in the art upon reference to the detailed description which hereinafter follows.

SUMMARY OF THE INVENTION

The invention provides for a hydrocyanation process comprising reacting an acyclic, aliphatic, monoethylenically unsaturated compound in which the ethylenic double bond is not conjugated to any other olefinic group in the molecule with a source of HCN in the presence of a catalyst precursor composition comprising a Lewis acid, a zero-valent nickel and at least one, multidentate phosphite ligand selected from the group represented by the following formulae I, I-A or I-B, in which all like reference characters have the same meaning, except as further explicitly limited.

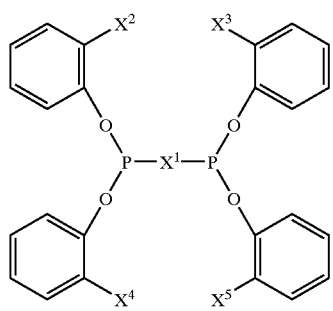

Formula I wherein $X^1$ is a bridging group selected from the group consisting of:

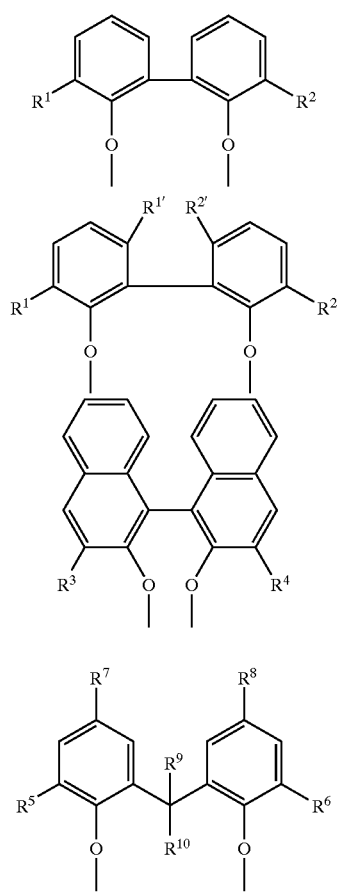

wherein $R^1$, $R^2$, $R^3$, $R^4$, $R^5$, $R^6$, $R^7$, $R^8$, $R^{1'}$, $R^{2'}$ are independently selected from the group consisting of H, $C_1$ to $C_{18}$ alkyl, cycloalkyl, trialkylsilyl, triarylsilyl, halogen, nitrile, perfluoroalkyl, —$SO_2R^{11}$, —$SO_2NR^{12}_2$, acetal, ketal, dialkylamnino, or diarylamino, —$OR^{11}$, —$CO_2R^{11}$, —$(CNR^{11})R^{11}$, —$(CNOR^{11})R^{11}$, wherein $R^{11}$ is $C_1$ to $C_{18}$ alkyl, aryl, or substituted aryl, —$C(O)R^{12}$, —$C(O)NR^{12}R^{13}$, —O—$C(O)R^{12}$, —$NR^{12}$—$C(O)R^{13}$, wherein $R^{12}$ and $R^{13}$ are independently selected from the group of H, $C_1$ to $C_{18}$ alkyl, cycloalkyl, aryl, or substituted aryl;

wherein positions other than $R^1$ through $R^8$ on the aromatic rings may also be substituted with $C_1$ to $C_{18}$ alkyl, cycloalkyl, trialkylsilyl, triarylsilyl, halogen, nitrile, perfluoroalkyl, sulfonyl, acetal, ketal, dialkylamino, diarylamino, —$OR^{11}$, —$CO_2R^{11}$, $RCNR^{11}$, or $RCNOR^{11}$, wherein $R^9$ and $R^{10}$ are independently selected from the group consisting of H, $C_1$ to $C_{18}$ alkyl, cycloalkyl, aryl, or substituted aryl;

wherein $X^2$ through $X^5$ are independently selected from the group consisting of:

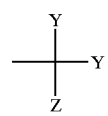

wherein Y is independently selected from the group consisting of H, aryl, $CR^{14}_3$, wherein $R^{14}$ is H, $C_1$–$C_{18}$ alkyl, cycoalkyl, or aryl, $(CR^{14}_2)_n$—$OR^{14}$, $(CR^{14}_2)_n$—$NHR^{15}$, wherein n=0–3, wherein $R^{15}$ is selected from the group consisting of H, alkyl, aryl, —$SO_2R^{11}$, —$SO_2NR^{12}_2$, —$COR^{16}$, wherein $R^{16}$ is H, $C_1$–$C_{18}$ alkyl, cycloalkyl, aryl or perfluoroalkyl;

and Z is selected from tile group consisting of $(CR^{14}_2)_n$—$OR^{14}$ wherein n=0–3 and $R^{14}$ is defined as above.

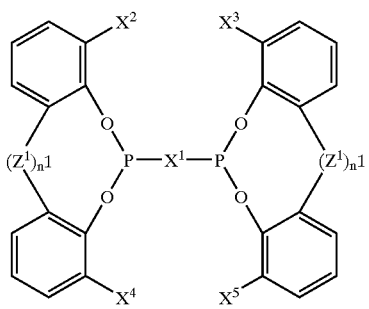

Formula I-A

In other embodiments of the invention a ligand of the structure of Formula I-A may be substituted for the ligand of Formula I, and in those embodiments an aromatic ring carbon in the ortho position to an O bonded to a P may be bonded through $(Z^1)n^1$ to another aromatic ring carbon in the ortho position to the other O bonded to the P;

wherein $Z^1$ is independently

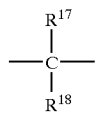

and each of $R^{17}$ and $R^{18}$ are independently selected from the group consisting of H, $C_1$ to $C_{18}$ alkyl, cycloalkyl, aryl, or substituted aryl, $n^1$ is either one or zero; and wherein it is understood that $n^1$=0 represents a bond replacing the two aromatic ring hydrogens.

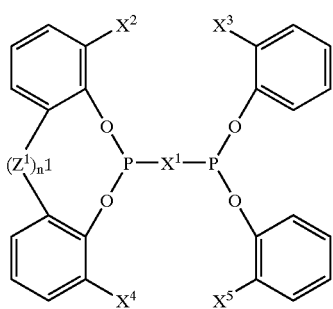

Formula I-B

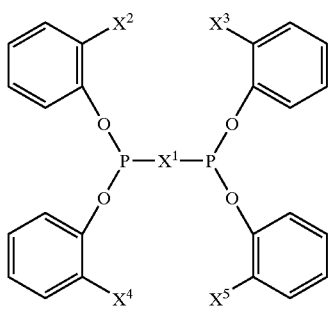

Formula II

In other embodiments of the invention a ligand of the structure of Formula I-B may be substituted for the ligand of Formula 1, and wherein an aromatic ring carbon in the ortho position to an O bonded to a P may be bonded through $(Z^1)n^1$ to another aromatic ring carbon in the ortho position to the other O bonded to the P;

wherein $Z^1$ is independently

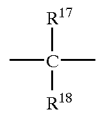

and each of $R^{17}$ and $R^{18}$ are independently selected from the group consisting of H, $C_1$ to $C_{18}$ alkyl, cycloalkyl, aryl, or substituted aryl, $n^1$ is either one or zero; and wherein it is understood that $n^1=0$ represents a bond replacing the two aromatic ring hydrogens.

Furthermore, in embodiments of the invention utilizing Formula I, Formula I-A or Formula I-B, either one of the Y's may be linked with Z to form a cyclic ether. In such embodiments, at least one of the groups $X^2$–$X^5$ may have the structure of formulae A or B wherein $Y^3$=O or $CH_2$; and $R^{14}$ is defined as above:

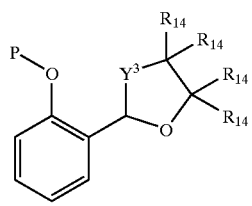

Formula A

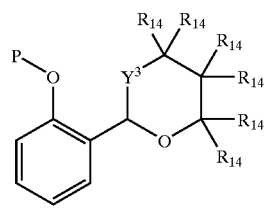

Formula B

The invention also provides for a multidentate phosphite ligand having the structure represented by the following Formula II, Formula II-A or Formula II-B in which all like reference characters have the same meaning, except as further explicitly limited.

wherein $X^1$ is a divalent bridging group and is selected from the group consisting of:

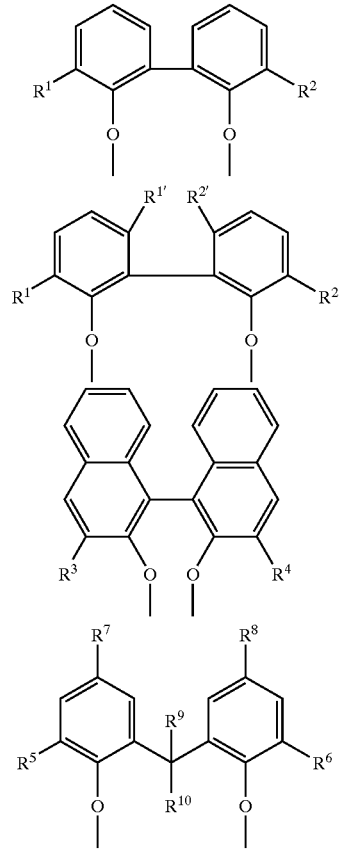

wherein $R_1$, $R_2$, $R_3$, $R^4$, $R^5$, $R^6$, $R^7$, $R_8$, $R_{1'}$, and $R^{2'}$ are independently selected from the group consisting of H, $C_1$ to $C_{18}$ alkyl, cycloalkyl, trialkylsilyl, triarylsilyl, halogen, nitrile, perfluoroalkyl, —$SO_2R_{11}$, —$SO_2NR_2{}^{12}$, acetal, ketal, dialkylamino, or diarylamino, —$OR^{11}$, —$CO_2R^{11}$, —$(CNR_{11})R_{11}$, —$(CNOR_{11})R_{11}$, wherein $R_{11}$ is $C_1$ to $C_{18}$ alkyl, cycloalkyl, aryl, or substituted aryl, —$C(O)R^{12}$, —$C(O)NR^{12}R^{13}$, —O—$C(O)R_{12}$, —$NR^{12}$—$C(O)R^{13}$, wherein $R^{12}$ and $R^{13}$ are independently selected from the group of H, $C_1$ to $C_{18}$ alkyl, cycloalkyl, aryl, or substituted aryl; wherein positions other than $R^1$ through $R^8$ on the aromatic rings may also be substituted with $C_1$ to $C_{18}$ alkyl, cycloalkyl, trialkylsilyl, triarylsilyl, halogen, nitrile, perfluoroalkyl, sulfonyl, acetal, ketal, dialkylamino, diarylamino, —$OR_{11}$, —$CO_2R_{11}$, R $CNR^{11}$, or $RCNOR^{11}$, wherein $R^9$ and $R_{10}$ are independently selected from the group consisting of H, $C_1$ to $C_{18}$ alkyl, cycloalkyl, aryl, or substituted aryl, wherein $X^2$ through $X^5$ are independently selected from the group consisting of:

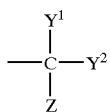

$Y^1$ is independently selected from the group consisting of H, aryl, $CR^{14}_3$, wherein $R^{14}$ is H, $C_1$–$C_{18}$ alkyl, cycloalkyl, or aryl, $(CR^{14}_2)_n$—$OR^{14}$, $(CR^{14}_2)_n$—$NHR^{15}$ wherein n=0–3, wherein $R^{15}$ is selected from the group consisting of H, alkyl, cycloalkyl, aryl, —$SO_2R^{11}$, —$SO_2NR^{12}_2$, —$COR^{16}$ wherein $R^{16}$ is H, $C_1$–$C_{18}$ alkyl, cycloalkyl, aryl, or perfluoroalkyl;

$Y^2$ is independently selected from the group consisting of aryl, $CR^{14}_3$, wherein $R^{14}$ is H, $C_1$–$C_{18}$ alkyl, cycloalkyl, or aryl, $(CR^{14}_2)_n$—$OR^{14}$, $(CR^{14}_2)_n$—$NHR^{15}$ wherein n=0–3, wherein $R^{15}$ is selected from the group consisting of H, alkyl, cycloalkyl, aryl, —$SO_2R^{11}$, —$SO_2NR^{12}_2$, —$COR^{16}$ wherein $R^{16}$ is H, $C_1$–$C_{18}$ alkyl, cycloalkyl, aryl, or perfluoroalkyl;

Z is selected from the group consisting of $(CR^{14}_2)_n$—$OR^{14}$ wherein n=0–3 and wherein $R^{14}$ is defined as above.

Formula II-A

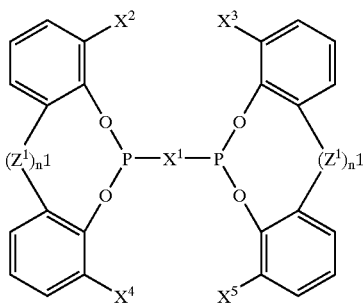

In other embodiments of the invention a ligand of the structure of Formula II-A may be substituted for the ligand of Formula II, and wherein an aromatic ring carbon in the ortho position to an O bonded to a P may be bonded through $(Z^1)n^1$ to another aromatic ring carbon in the ortho position to the other O bonded to the P;

wherein $Z^1$ is independently

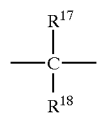

and each $R^{17}$ and $R^{18}$ are independently selected from the group consisting of H, $C_1$ to $C_{18}$ alkyl, cycloalkyl, aryl, or substituted aryl, $n^1$ is either one or zero; and wherein it is understood that $n^1$=0 represents a bond replacing the two aromatic ring hydrogens.

Formula II-B

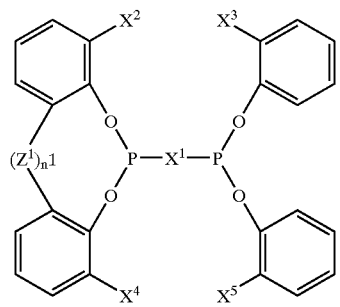

In other embodiments of the invention a ligand of the structure of Formula II-B may be substituted for the ligand of Formula II, and an aromatic ring carbon in the ortho position to an O bonded to a P maybe bonded through $(Z^1)n^1$ to another aromatic ring carbon in the ortho position to the other O bonded to the P;

wherein $Z^1$ is independently

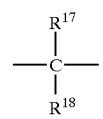

and each $R^{17}$ and $R^{18}$ are independently selected from the group consisting of H, $C_1$ to $C_{18}$ alkyl, cycloalkyl, aryl, or substituted aryl, $n^1$ is either one or zero; and wherein it is understood that $n^1$=0 represents a bond replacing the two aromatic ring hydrogens.

Furthermore, in embodiments of the invention utilizing Formula II, Formula II-A or Formula II-B, either $Y^1$ or $Y^2$ may be linked with Z to form a cyclic ether. In such embodiments, at least one of the groups $X^2$–$X^5$ may have the structure of formulae A or B wherein $Y^3$=O or $CH_2$; and $R^{14}$ is defined as above:

Formula A

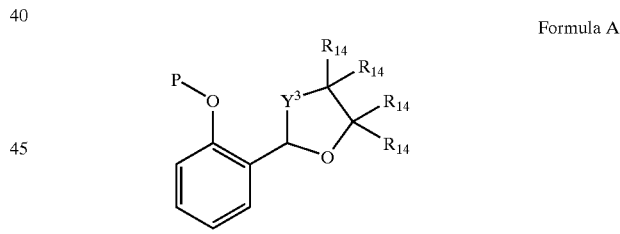

Formula B

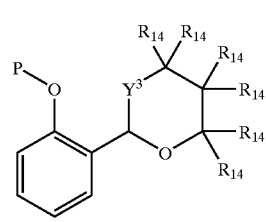

The invention also provides for certain multidentate phosphite ligands and catalyst compositions made therefrom useful in the hydrocyanation of diolefinic compounds to produce nonconjugated acyclic nitriles as well as a liquid phase process for the isomerization of those nitriles to 3- and/or 4-monoalkene linear nitriles. In particular, these include the ligands of Formula II, Formula I-A and Formula II-B in combination with nickel.

The present invention further provides for an improved process for the hydrocyanation of diolefinis, such as butadiene, and the isomerization of nonconjugated acyclic nitrites. The present invention further provides for an improved process for the hydrocyanation of diolefins without the need for Lewis acid promoters. The multidentate phosphite ligands in these embodiments include the ligands of Formula II, Formula II-A and Formula II-B in combination with nickel wherein the ligands have heteroatom-containing substituents on the carbon attached at the ortho position of the terminal phenol groups. The present invention may also provide a catalyst having a high degree of selectivity in the hydrocyanation of diolefins such that no additional isomerization step is required.

Specifically, the present invention provides an improved process for the liquid phase hydrocyanation of diolefins and isomerization of the resulting nonconjugated acyclic nitrites comprising, reacting an acyclic aliphatic diolefin, preferably butadiene, with a source of HCN, wherein the process comprises conducting the hydrocyanation and/or isomerization in the presence of a catalyst composition comprising zero-valent nickel and at least one multidentate phosphite ligand selected from the group represented by formulae II, II-A and II-B as set forth above, in which all like reference characters have the same meaning, except as further explicitly limited:

The reactions are most conveniently performed continuously from hydrocyanation of the starting diolefin to the final 3- and/or 4-monoalkene linear nitrites. However, the processes can be conducted stepwise, i.e., the nonconjugated acyclic nitriles resulting from the hydrocyanation can be isolated per se, prior to isomerization. Furthermore, nonconjugated acyclic nitrites prepared by any method can be used as starting materials for the isomerization in accordance with this invention.

DETAILED DESCRIPTION OF THE PREFERRED EMBODIMENTS

The invention provides for certain multidentate phosphite ligands, improved catalyst systems employing such ligands, and the use of such multidentate phosphite ligands in, for example, hydrocyanation and/or isomerization reactions. The multidentate phosphite ligands of the invention and catalyst systems employing such ligands have a broad range of applicability to various other catalytic reactions such as hydroformylation and may be optimized for such reactions in accordance with the present invention.

The catalyst compositions useful in the invention preferably are comprised of a multidentate phosphite ligand and a transition metal.

The divalent bridging compounds used in the ligands described in formulae I, I-A, I-B, II, II-A, and II-B may be prepared by a variety of methods known in the art. For example, dimethyl 2,2'-dihydroxyl-1,1'-binaphthalene-3,3'-dicarboxylate can be prepared according to *J. Am. Chem. Soc.*, 1954, 76, 296 or in *Tetrahedron Lett.*, 1990, 413 and *Org. Proc. Prep. International*, 1991, 23, 200; 2,2'-ethylidenebis(4,6-dimethylphenol) can be prepared according to *Bull. Chem. Soc,: Japn.*, 1989, 62, 3603; 3,3',5,5'-tetramethyl-2,2'-biphenol can be prepared according to *J. Org. Chem.*, 1963,28, 1063; 2,2'-dihydroxy-3,3'-dimethoxy-5,5'-dimethyl-1,1'-biphenylene can be prepared according to *Phytochemistry*, 1988, 27, 3008; and 3,3'-dimethyl-2,2'-dihydroxydiphenylmethane can be prepared according to *Synthesis*, 1981, 2, 143. 3,3',5,5',6,6'-Hexamethyl-2,2'-biphenol can be prepared according to JP 85-216749.

Acetal substituted salicylaldehydes can be prepared by those skilled in the art. For example, an acetal can be prepared by refluxing a glycol with salicylaldehyde in the presence of oxalic acid catalyst. For references for preparing acetals by the acid catalyzed reaction of an aldehyde and an alcohol, see *Tetrahedron*, 1996, 14599; *Tet. Lett.*, 1989, 1609; *Tetrahedron*, 1990, 3315. Cyclic ether substituted phenols can be prepared as described in *Aust. J. Chem.* 1988, 41, 69–80.

Phosphorochloridite may be prepared by a variety of methods known in the art, for example, see descriptions in *Polymer*, 1992, 33, 161; *Inorganic Synthesis*, 1966, 8, 68; U.S. Pat. No. 5,210,260; *Z. Anorg. Allg. Chem.*, 1986, 535, 221. With ortho-substituted phenols, phosphorochloridites can be prepared in situ from $PCl_3$ and the phenol. Also, phosphorochloridites of 1-naphthols can be prepared in situ from $PCl_3$ and 1-naphthols in the presence of a base like triethylamine. Another process for preparing the phosphochlorodite comprises treatment of N,N-alkyl diarylphosphoramidite with HCl. $ClP(OMe)_2$ has been prepared in this manner, see *Z. Naturforsch*, 1972, 27B, 1429. Phosphorochloridites derived from substituted phenols have been prepared using this procedure as described in commonly assigned U.S. Pat. No. 5,821,378.

By contacting the thus obtained $(OAr)_2PCl$, wherein Ar is a substituted aryl, with a divalent bridging compound, for example by the method described in U.S. Pat. No. 5,235,113, a bidentate phosphite ligand is obtained which can be used in the process according to the invention.

Bis(phosphite) ligands supported on polymer resins such as Merrifield's resin can be prepared by similar methods, such as those described in Hetet, C. L., David, M., Carreaux, F., Carboni, B. and Sauleau, A., *Tetrahedron Lett.*, 1997, 38, 5153–5156, and Gisin, B. F. *Helv. Chim. Acta* 1973, 56, 1476–1482.

The transition metal may be any transition metal capable of carrying out catalytic transformations and may additionally contain labile ligands which are either displaced during the catalytic reaction, or take an active part in the catalytic transformation. Any of the transition metals may be considered in this regard. The preferred metals are those comprising group VIII of the Periodic Table. The preferred metals for hydroformylation are rhodium, cobalt, iridium, ruthenium, palladium and platinum. The preferred metals for hydrocyanation and/or isomerization are nickel, cobalt, and palladium, and nickel is especially preferred for hydrocyanation.

The catalyst compositions of the invention are comprised of at least one multidentate phosphite ligand according to any one of formulae I, I-A, I-B, II, II-A, and II-B and a transition metal. In embodiments of the invention, catalyst compositions useful for processes such as hydroformylation may have Group VIII compounds such as can be prepared or generated according to techniques well known in the art, as described, for example, WO 95 30680, U.S. Pat. No. 3,907, 847, and *J. Amer. Chem. Soc.*, 1993, 115, 2066. Examples of such suitable Group VIII metals are ruthenium, rhodium, and iridium. Suitable Group VIII metal compounds are hydrides, halides, organic acid salts, acetylacetonates, inorganic acid salts, oxides, carbonyl compounds and amine compounds of these metals. Examples of suitable Group VIII metal compounds are, for example, $Ru_3(CO)_{12}$, $Ru(NO_3)_2$, $RuCl_3(Ph_3P)_3$, $Ru(acac)_3$, $Ir_4(CO)_{12}$, $IrSO_4$, $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]_2$, and $[RhCl(COD)]_2$ (wherein "acac" is an acetylacetonate group; "OAc" is an acetyl group; "COD" is 1,5-cyclooctadiene; and "Ph" is a phenyl group). However, it should be noted that the Group VIII metal compounds are not necessarily limited to the above listed compounds. The Group VIII metal is preferably rhodium. Rhodium compounds that contain ligands which can be displaced by the multidentate phosphites are a preferred source of rhodium. Examples of such preferred rhodium compounds are $Rh(CO)_2$ (acetylacetonate), $Rh(CO)_2(C_4H_9COCHCO\text{-}t\text{-}C_4H_9)$, $Rh_2O_3$, $Rh_4(CO)_{12}$, $Rh_6(CO)_{16}$, $Rh(O_2CCH_3)_2$, and Rh(2-ethylhexanoate). Rhodium supported on carbon may also be used in this respect.

Nickel compounds can be prepared or generated according to techniques well known in the art, as described, for example, in U.S. Pat. Nos. 3,496,217; 3,631,191; 3,846,461; 3,847,959; and 3,903,120, which are incorporated herein by reference. Zero-valent nickel compounds that contain ligands which can be displaced by the organophosphorus ligand are a preferred source of nickel. Two such preferred zero-valent nickel compounds are $Ni(COD)_2$ (COD is 1,5-cyclooctadiene) and $Ni\{P(O\text{-}o\text{-}C_6H_4CH_3)_3\}_2(C_2H_4)$, both of which are known in the art. Alternatively, divalent nickel compounds may be combined with a reducing agent, to serve as a source of nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120, is also a suitable source of zero-valent nickel.

Depending upon the desired reaction to be performed, the catalyst composition of this invention may also include the presence of one or more Lewis acid promoters, which affect both the activity and the selectivity of the catalyst system. The promoter maybe an inorganic or organometallic compound in which the at least one of the elements of said inorganic or organometallic compound is selected from scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, (iso-$C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$. Suitable promoters are further described in U.S. Pat. Nos. 3,496,217; 3,496,218; and 4,774,353. These include metal salts (such as $ZnCl_2$, $CoI_2$, and $SnCl_2$), and organometallic compounds (such as $RAlCl_2$, $R_3SnO_3SCF_3$, and $R_3B$, where R is an alkyl or aryl group). U.S. Pat. Nos. 4,874,884 describes how synergistic combinations of promoters can be chosen to increase the catalytic activity of the catalyst system. Preferred promoters include $CdCl_2$, $FeCl_2$, $ZnCl_2$, $B(C_6H_5)_3$, and $(C_6H_5)_3SnX$, where $X=CF_3SO_3$, $CH_3C_6H_5SO_3$, or $(C_6H_5)_3BCN$. The mole ratio of promoter to nickel present in the reaction can be within the range of about 1:16 to about 50:1.

Hydrocyanation of Monoolefinic Compounds

The present invention provides for a process of hydrocyanation, comprising reacting an unsaturated compound with a source of hydrogen cyanide in the presence of a catalyst composition comprising a transition metal selected from Ni, Co, and Pd, and a Lewis acid compound, and at least one ligand selected from the group represented by formulae I, I-A, I-B, II, II-A or II-B Representative ethylenically unsaturated compounds which are useful in the hydrocyanation process of this invention are shown in Formulae III or V, and the corresponding terminal nitrile compounds produced are illustrated by Formulae IV or VI, respectively, wherein like reference characters have same meaning.

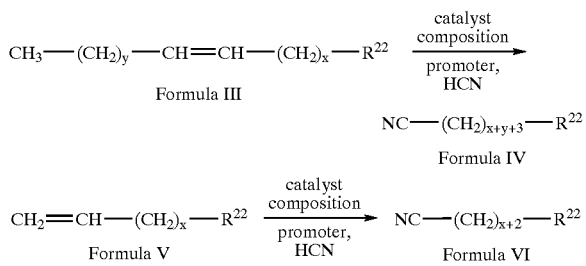

wherein
$R^{22}$ is H, CN, $CO_2R^{23}$, or perfluoroalkyl;
y is an integer of 0 to 12;
x is an integer of 0 to 12 when $R^{22}$ is H, $CO_2R^{23}$ or perfluoroalkyl;
x is an integer of 1 to 12 when $R^{22}$ is CN; and
$R^{23}$ is $C_1$ to $C_{12}$ alkyl, or aryl.

The nonconjugated acyclic, aliphatic, monoethylenically unsaturated starting materials useful in this invention include unsaturated organic compounds containing from 2 to approximately 30 carbon atoms. Suitable unsaturated compounds include unsubstituted hydrocarbons as well as hydrocarbons substituted with groups which do not attack the catalyst, such as cyano. Examples of these monoethylenically unsaturated compounds include ethylene, propylene, 1-butene, 2-pentene, 2-hexene, etc., nonconjugated diethylenically unsaturated compounds such as allene, substituted compounds such as 3-pentenenitrile, 4-pentenenitrile, methyl pent-3-enoate, and ethylenically unsaturated compounds having perfluoroalkyl substituents such as, for example, $C_zF_{2z+1}$, where z is an integer of up to 20. The monoethylenically unsaturated compounds may also be conjugated to an ester group such as methyl pent-2-enoate.

Preferred are nonconjugated linear alkenes, nonconjugated linear allene-nitriles, nonconjugated linear alkenoates, linear alk-2-enoates and perfluoroalkyl ethylenes. Most preferred substrates include 3- and 4-pentenenitrile, alkyl 2-, 3-, and 4-pentenoates, and $C_zF_{2z+1}CH=CH_2$ (where z is 1 to 12).

3-Pentenenitrile and 4-pentenenitrile are especially preferred. As a practical matter, when the nonconjugated acyclic aliphatic monoethylenically unsaturated compounds are used in accordance with this invention, up to about 10% by weight of the monoethylenically unsaturated compound may be present in the form of a conjugated isomer, which itself may undergo hydrocyanation. For example, when 3-pentenenitrile is used, as much as 10% by weight thereof may be 2-pentenenitrile. (As used herein, the term "pentenenitrile" is intended to be identical with "cyanobutene").

The preferred products are terminal alkanenitriles, linear dicyanoalkylenes, linear aliphatic cyanoesters, and 3-(perfluoroalkyl)propionitrile. Most preferred products are adiponitrile, alkyl 5-cyanovalerate, and $C_zF_{2z+1}CH_2CH_2CN$, where z is 1 to 12.

The present hydrocyanation process may be carried out, for example, by charging a reactor with the reactants, catalyst composition, and solvent, if any; but preferably, the hydrogen cyanide is added slowly to the mixture of the other components of the reaction. Hydrogen cyanide may be delivered as a liquid or as a vapor to the reaction. Another suitable technique is to charge the reactor with the catalyst and the solvent to be used, and feed both the unsaturated compound and the HCN slowly to the reaction mixture. The molar ratio of unsaturated compound to catalyst can be varied from about 10:1 to about 2000:1.

Preferably, the reaction medium is agitated, for example, by stirring or shaking. The reaction product can be recovered by conventional techniques such as, for example, by distillation. The reaction may be run either batchwise or in a continuous manner.

The hydrocyanation reaction can be carried out with or without a solvent. The solvent, if used, should be liquid at the reaction temperature and pressure and inert towards the unsaturated compound and the catalyst. Suitable solvents include hydrocarbons, such as benzene or xylene, and nitrites, such as acetonitrile or benzonitrile. In some cases, the unsaturated compound to be hydrocyanated may itself serve as the solvent.

The exact temperature is dependent to a certain extent on the particular catalyst being used, the particular unsaturated compound being used and the desired rate. Normally, temperatures of from −25° C. to 200° C. can be used, the range of 0° C. to 150° C. being preferred.

Atmospheric pressure is satisfactory for carrying out the present invention and hence pressures of from about 0.05 to 10 atmospheres (50.6 to 1013 kPa) are preferred. Higher pressures, up to 10,000 kPa or more, can be used, if desired, but any benefit that may be obtained thereby would probably not justify the increased cost of such operations.

HCN can be introduced to the reaction as a vapor or liquid. As an alternative, a cyanohydrin can be used as the source of HCN. See, for example, U.S. Pat. No. 3,655,723.

The process of this invention is carried out in the presence of one or more Lewis acid promoters which affect both the activity and the selectivity of the catalyst system. The promoter may be an inorganic or organometallic compound in which the in which the at least one of the elements of said inorganic or organometallic compound is selected from scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, (iso-$C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$. Suitable promoters are further described in U.S. Pat. Nos. 3,496,217; 3,496,218; and 4,774,353. These include; metal salts (such as $ZnCl_2$, $CoI_2$, and $SnCl_2$), and organometallic compounds. (such as $RAlCl_2$, $R_3SnO_3SCF_3$, and $R_3B$, where R is an alkyl or aryl group). U.S. Pat. No. 4,874,884 describes how synergistic combinations of promoters can be chosen to increase the catalytic activity of the catalyst system. Preferred promoters include $CdCl_2$, $FeCl_2$, $ZnCl_2$, $B(C_6H_5)_3$, and $(C_6H_5)_3SnX$, where $X=CF_3SO_3$, $CH_3C_6H_5SO_3$, or $(C_6H_5)_3BCN$. The mole ratio of promoter to nickel present in the reaction can be within the range of about 1:16 to about 50:1.

Hydrocyanation with Subsequent Isomerization

The present invention also provides for a process for the hydrocyanation of diolefins, which comprises reacting a diolefin with a source of hydrogen cyanide in the presence of a catalyst composition comprising a transition metal selected from Ni, Co, and Pd, and at least one ligand selected from the group represented by Formula II, II-A, or II-B. In addition, this invention provides for a process for the isomerization of branched monoalkenenitriles to linear monoalkene nitrites in the presence of a catalyst composition comprising a transition metal selected from Ni, Co, and Pd, and a ligand selected from the group represented by Formula II, II-A, or II-B.

The diolefins used in this invention include primarily conjugated diolefins containing from 4 to 10 carbon atoms; for example, 1,3-butadiene (BD) and cis and trans-2,4-hexadienes. Butadiene is especially preferred by reason of its commercial importance in the production of adiponitrile. Other suitable diolefins include diolefins substituted with groups which do not deactivate the catalyst, for example, cis and trans-1,3-pentadienes.

The following formulas VII and VII illustrate suitable representative starting diolefinic compounds; and formulas IX, X, and XI represent the products obtained from 1,3-butadiene and HCN.

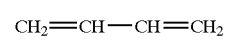

1,3-butadiene

VII

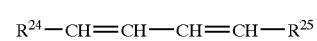

VIII wherein each one of $R^{24}$ and $R^{25}$, independently, is H or a $C_1$ to $C_3$ alkyl.

3PN

IX

4PN

X

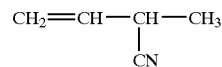

2M3

XI

It will be recognized that Compound VII is a special case of formula VIII, where each one of $R^{24}$ and $R^{25}$ is hydrogen. In formulas IX, X, and XI, 3PN is 3-pentenenitrile, 4PN is 4-pentenenitrile, and 2M3 is 2-methyl-3-butenenitrile.

In the practice of the hydrocyanation of the diolefin in accordance with the present invention, the following description applies:

The hydrocyanation reaction can be carried out with or without a solvent. The solvent should be a liquid at the reaction temperature and inert towards the unsaturated compound and the catalyst. Generally, such solvents are hydrocarbons such as benzene, xylene, or nitrites such as acetonitrile, benzonitrile, or adiponitrile.

The exact temperature used is dependent, to a certain extent, on the particular catalyst being used, the particular unsaturated compound being used and the desired rate. Generally, temperatures of from −25° C. to 200° C., can be used with from 0° C. to 150° C., being the preferred range.

The reaction may be carried out by charging a reactor with all of the reactants or preferably the reactor is charged with the catalyst or catalyst components, the unsaturated compound, and solvent. Hydrogen cyanide gas is then swept over the surface of the reaction mixture or bubbled through said reaction mixture. If desired, when using a gaseous unsaturated organic compound, the hydrogen cyanide and the unsaturated organic compound may be fed together into the reaction medium. The molar ratio of HCN to catalyst generally is varied from about 10:1 to 100,000:1, preferably 100:1 to 5,000:1, for a batch operation. In a continuous operation, such as when using a fixed bed catalyst type of operation, a higher proportion of catalyst may be used such as 5:1 to 100,000:1, preferably 100:1 to 5,000:1, HCN to catalyst.

Preferably, the reaction mixture is agitated, such as by stirring or shaking. The cyanated product can be recovered by conventional techniques such as a crystallization of the product from solution or by distillation.

One can either isolate the 2-alkyl-3-monoalkenenitriles produced by the hydrocyanation of the diolefin or proceed with the isomerization under similar reaction conditions.

The 2-alkyl-3-monoalkenenitriles used as the starting materials in the isomerization of this invention can result from the hydrocyanation of diolefin described above or can come from any other available source. Suitable starting 2-alkyl-3-monoalkenenitriles can also carry groups which do not attack the catalyst, for example, another cyano group. Preferably, the starting 2-alkyl-3-monoalkenenitriles contain from 5 to 8 carbon atoms, excluding any additional substitution. 2-Methyl-3-butenenitrile (2M3) is especially important in the production of adiponitrile. Other representative nitrites include 2-ethyl-3-butenenitrile and 2-propyl-3-butenenitrile.

The following formulas XI and XII illustrate suitable representative starting 2-alkyl-3-monoalkenenitriles. When the starting nitrile is 2-methyl-3-butenenitrile, the isomerization products are 3-pentenenitrile and 4-pentenenitrile.

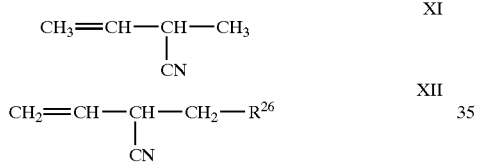

wherein $R^{26}$ is H or a $C_1$ to $C_3$ alkyl.

It will be recognized that Formula XI is a special case of Formula XII, where $R^{26}$ is hydrogen.

The isomerization process of this invention can be carried out, for example, at atmospheric pressure and at any temperature in the range of 10–200° C., preferably in the range 60–150° C. The pressure is not critical, however, and can be above or below atmospheric pressure if desired. Any of the conventional batch or continuous flow procedures may be used either in the liquid phase or, with volatile reactants and products, in the vapor phase. The reactor may be of any mechanically and chemically resistant material, and is usually of glass or an inert metal or alloy, e.g., nickel, copper, silver, gold, platinum, stainless steel, Monel®, Hastelloy®, etc.

The process is usually carried out "neat", i.e., without an added diluent or solvent; any solvent or diluent that is nondestructive of the catalyst can be used. Suitable solvents include aliphatic or aromatic hydrocarbons (hexane, cyclohexane, benzene), ethers (diethyl ether, tetrahydrofuran (THF), dioxane, glycol dimethyl ether, anisole), esters (ethyl acetate, methyl benzoate), nitrites (acetonitrile, benzonitrile), etc.

A nonoxidizing environment is desirable in order to retard oxidative deactivation of the catalyst. Accordingly, an inert atmosphere, e.g., nitrogen, is normally and preferably used, although air may be used if desired at the expense of loss of a proportion of the catalyst through oxidation.

The nickel complex is essentially nonvolatile, whereas the 2-alkyl-3-monoalkenenitrile reactant and the linear monoalkenenitrile products are relatively volatile. Accordingly, in a continuous flow procedure the catalyst may be a component of the flowing system in a completely liquid-phase operation, it may be in a mobile nonflowing liquid state in a semi-vapor phase operation, or it may be in a fixed-bed state (usually on a solid support) in a conventional flowing vapor-phase operation.

The time element in the process is not critical, and may generally be governed by practical considerations. The time required for a practical level of conversion of 2-alkyl-3-monoalkenenitrile to linear monoalkenenitrile is dependent upon the temperature of reaction, i.e., operation at lower temperature generally requires a longer time than operation at a higher temperature. A practical reaction time can be in the range of a few seconds to many hours, depending on the particular conditions and method of operation.

The molar ratio of 2-alkyl-3-monoalkenenitrile to catalyst is generally greater than 1:1, usually in the range from about 5:1 to 20,000:1, preferably 100:1 to 5,000:1, for a batch or continuous operation.

The invention will now be illustrated by the following non-limiting examples of certain embodiments thereof, wherein all parts, proportions, and percentages are by weight, unless otherwise indicated.

The following definitions are applicable wherever the defined terms appear in this specification:

The term "hydrocarbyl" designates a hydrocarbon molecule from which one hydrogen atom has been removed. Such molecules can contain single, double or triple bonds.

3PN: 3-pentenenitrile

2PN: 2-pentenenitrile

4PN: 4-pentenenitrile

2M3: 2-methyl-3-butenenitrile

VN: valeronitrile

ESN: ethylsuccinonitrile

MGN: 2-methylglutaronitrile

5FVN: 5-formylvaleronitrile

M3P: methyl 3-pentenoate

BD: 1,3-butadiene

COD: 1,5-cyclooctadiene $Et_3N$: triethylamine $PCl_3$: phosphorus trichloride

THF: tetrahydrofuran

The protocol for calculating certain reaction results for hydrocyanation reactions and isomerization reactions follows:

For step 1 hydrocyanation reactions the % useful pentenenitriles (PN's) and the 3PN/2M3 ratio is reported. The product distribution is analyzed by gas chromatograph using valeronitrile as an internal standard. The % useful PN's is the molar ratio of the sum of 3PN(cis and trans) and 2M3 divided by the amount of HCN. The 3PN/2M3 ratio is the ratio of cis and trans 3PN to 2M3.

For isomerization reactions the 3PN/2M3 ratio is reported and is defined as above.

For step 2 hydrocyanation reactions the selectivity to adiponitrile (ADN) is ADN/(ESN+MGN+ADN). The 3PN and 4PN conversion is calculated using 2-ethoxyethylether (EEE) as an internal standard. The total conversion of PN's to dinitriles (DN's) based on the assumption that all material is accounted for, is calculated as (sum (mol DN's)/sum (PN's+BN's+DN's)). (BN's are butenenitriles). The conversion based on HCN is calculated by dividing the total conversion of PN's to DN's by the HCN/PN ratio in the original feed, i.e., (mol DN/mol PN at start)/(mol HCN/mol PN at start).

EXAMPLE 1

Synthesis of Acetal A

Salicylaldehyde (24.4 g, 200 mmol), ethylene glycol (31 g, 500 mmol), oxalic acid (1 g, 11 mmol), and toluene (150 mL) were combined and heated to reflux for 3 days in an apparatus equipped with a condenser and a Dean-Stark trap. After cooling, the solution was washed with NaHCO$_3$ and distilled water. The solution was dried over MgSO$_4$, and the solvent was evaporated to give 26 g of an off white solid. It was crystallized from hexane.

EXAMPLE 2

Synthesis of Acetal B

Salicylaldehyde (244 g, 2.0 mol); 1,3-propanediol (228 g, 3.0 mol), and oxalic acid (4.5 g, 0.05 mol) were added to 400 mL toluene and heated to reflux for 8 hours in an apparatus equipped with a condenser and a Dean-Stark trap. After cooling, the solution was washed with NaHCO$_3$ and distilled water, and the solution was dried over MgSO$_4$. The product precipitated when the solvent was being evaporated. The solid was collected and dissolved in hot hexane. The solution was filtered through Celite® (a filter aid manufactured by Johns Manville Corp.), and the product was crystallized to give 108 g of an off-white solid.

EXAMPLE 3

Synthesis of Acetal C

Salicylaldehyde (24 g, 0.2 mol), neopentyl glycol (20.9 g, 0.2 mol), oxalic acid (1 g, 11 mmol), and toluene (150 mL) were combined and heated to reflux for 2 days in an apparatus equipped with a condenser and a Dean-Stark trap. After cooling, the solution was washed with NaHCO$_3$ and distilled water. The solution was dried over MgSO$_4$, and the solvent was evaporated to give 39 g of a white solid, which was crystallized from hexane.

EXAMPLE 4

Synthesis of Acetal D

Salicylaldehyde (12.2 g, 0.1 mol) and trimethylorthoformate (10.6 g, 0.1 mol) were dissolved in dry MeOH (40 mL), and H$_2$SO$_4$ (0.25 g) was added. The reaction was stirred for 2 days under nitrogen at room temperature. The reaction was quenched by adding solid NaHCO$_3$ followed by Na$_2$CO$_3$ until the mixture became pH 9 or higher. The product was vacuum distilled (86.5–88° C., 2 torr), and 3.98 g of material was collected.

EXAMPLE 5

Synthesis of Amino-acetal E

Salicylaldehyde (6.11 g, 0.05 mol), 2-anilinoethanol (8.23 g, 0.06 mol), and oxalic acid (0.45 g, 5 mmol) were dissolved in toluene (50 mL) and heated to reflux overnight in an apparatus equipped with a condenser and a Dean-Stark trap. After cooling, the solution was washed with aqueous NaHCO$_3$, distilled water, and the toluene solution was dried over MgSO$_4$. After filtration, hexane was added until the product began to precipitate. 5.89 g of solid was collected.

EXAMPLE 6

Synthesis of Acetal F

A 300 mL flask was charged with 14.929 g of 5-chlorosalicylaldehyde, 12.409 g of pinacol and 0.300 g of oxalic acid and 150 mL of toluene. The flask was connected to a Dean-Starke trap and the mixture refluxed overnight. The mixture was washed with aqueous sodium bicarbonate and the organic layer was dried over magnesium sulfate. The solvent was removed by rotary evaporation. A yellow solid was obtained which was recrystallized from hot hexane. The solid was washed with acetonitrile to give 7.118 g of white solid. $^1$H NMR (500 MHz, C$_6$D$_6$, δ): 7.9 (s, 1H), 7.17 (d, 2.6 Hz, 1H), 7.08 (dd, J=2.6, 8.7 Hz, 1H), 6.73 (d, J=8.7 Hz, 1H), 6.02 (s, 1H), 1.26 (s, 6H0; 1.18 (s, 6H).

EXAMPLE 7

Synthesis of Acetal G

A flask was charged with 18 g of 5-chlorosalicylaldehyde, 13 g of 1,3-propanediol and 2 g of oxalic acid and 200 mL of toluene. The flask was connected to a Dean-Stark trap and the mixture refluxed for 12 hours. The mixture was washed with water and aqueous sodium bicarbonate. The organic layer was dried over magnesium sulfate and the solvent removed by rotary evaporation. A light brown oil was obtained (22.3 g) which solidified upon standing. $^1$H NMR (500 MHz, C$_6$D$_6$, δ): 7.7 (s, 1H), 6.96 (d, 2.6 Hz, 1H), 6.72 (dd, J=2.6, 8.7 Hz, 1H), 6.49 (d, J=8.7 Hz, 1H), 4.87(s, 1H), 3.37 (m, 2H), 2.99 (m, 2H), 1.37 (m, 1H), 0.35 (m, 1H).

EXAMPLE 8

Synthesis of Acetal H

Salicylaldehyde (24 g, 0.2 mol), 2-methyl-1,3-propanediol (18.0 g, 0.2 mol), oxalic acid (2.0 g), and toluene (250 mL) were combined and heated to reflux for 2 days in an apparatus equipped with a condenser and a Dean-Stark trap. After cooling, the solution was washed with NaHCO$_3$ (2×30 mL) and distilled water (30 mL). The solution was dried over MgSO$_4$, and the solvent was evaporated to give 39 g of a white solid, which was crystallized from hexane.

EXAMPLE 9

Synthesis of Ligand A

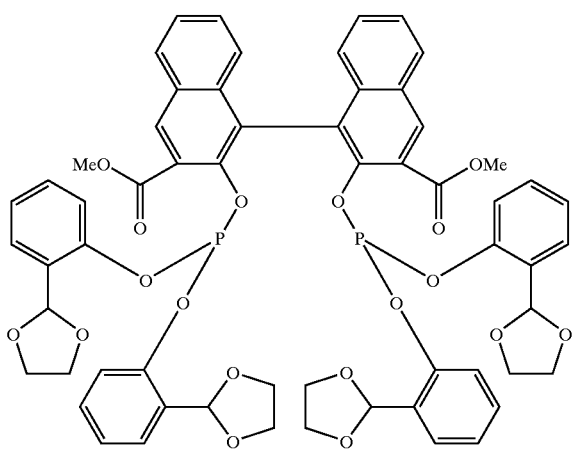

Acetal A (1.33 g, 8.0 mmol) and PCl$_3$ (0.55 g, 4 mmol) were dissolved in toluene (40 mL) and the solution was cooled to −40° C. Et$_3$N (1.0 g, 10.0 mmol) in toluene (15 mL) was added dropwise with stirring. The reaction was allowed to slowly warm to room temperature then stirred overnight. A mixture of Et$_3$N (0.4 g, 4.0 mmol) and dimethyl 2,2'-dihydroxy-1,1'-binaphthalene-3,3'-dicarboxylate (0.8 g, 2.0 mmol) in toluene (15 mL) was added to the phosphorochloridite solution, and the mixture was stirred for 2 hours. The solution was filtered through Celite®, and the solvent was removed to give 2.0 g of product. $^{31}$P NMR (C$_6$D$_6$): δ 132.6, other peaks at 146.3, 130.3, 130.7 ppm.

EXAMPLE 10

Synthesis of Ligand B

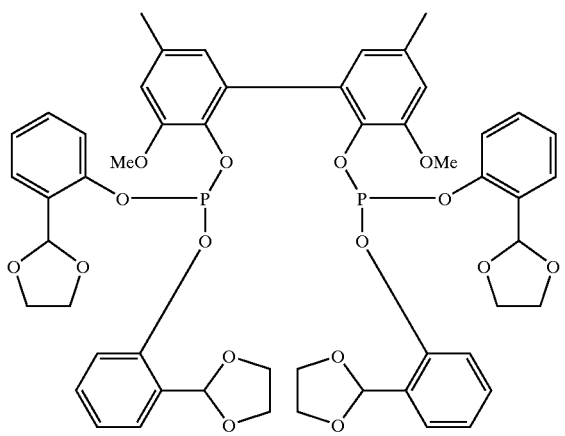

Acetal A (1.33 g, 8.0 mmol) and PCl$_3$ (0.55 g, 4 mmol) were dissolved in toluene (40 mL) and the solution was cooled to −40° C. Et$_3$N (1.0 g, 1.0.0 mmol) in toluene (15 mL) was added dropwise with stirring. The reaction was allowed to slowly warm to room temperature then stirred overnight. A mixture of Et$_3$N (0.4 g, 4.0 mmol) and 3,3'-dimethoxy-5,5'-dimethyl-2,2'-biphenol (0.55 g, 2.0 mmol) in toluene (15 mL) was added to the phosphorochloridite solution, and the mixture was stirred for 2 hours. The solution was filtered through Celite®, and the solvent was evaporated to give 1.8 g of product. $^{31}$P NMR (C$_6$D$_6$): δ 134.9, minor peaks at 145.4, 132.3 ppm.

EXAMPLE 11

Synthesis of Ligand C

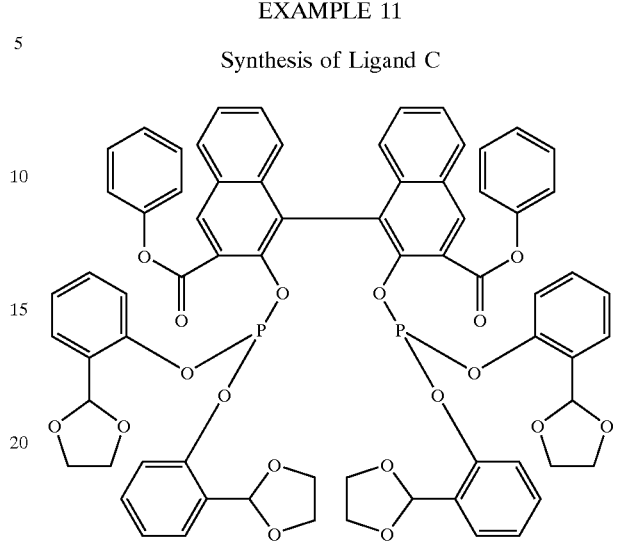

Acetal A (1.33 g, 8.0 mmol) and PCl$_3$ (0.55 g, 4 mmol) were dissolved in toluene (40 mL) and the solution was cooled to −40° C. Et$_3$N (1.0 g, 10.0 mmol) in toluene (15 mL) was added dropwise with stirring. The reaction was allowed to slowly warn to room temperature then stirred overnight. A mixture of Et$_3$N (0.4 g, 4.0 mmol) and diphenyl 2,2'-dihydroxy-1,1'-binaphthalene-3,3'-dicarboxylate (1.05 g, 2.0 mmol) in toluene (15 mL) was added to the phosphorochloridite solution, and the mixture was stirred for 2 hours. The solution was filtered through Celite®, and the solvent was removed to give 2.2 g of product. $^{31}$P NMR (C$_6$D$_6$): δ 130.2, minor peaks at 146.8, 131.4 ppm.

EXAMPLE 12

Synthesis of Ligand D

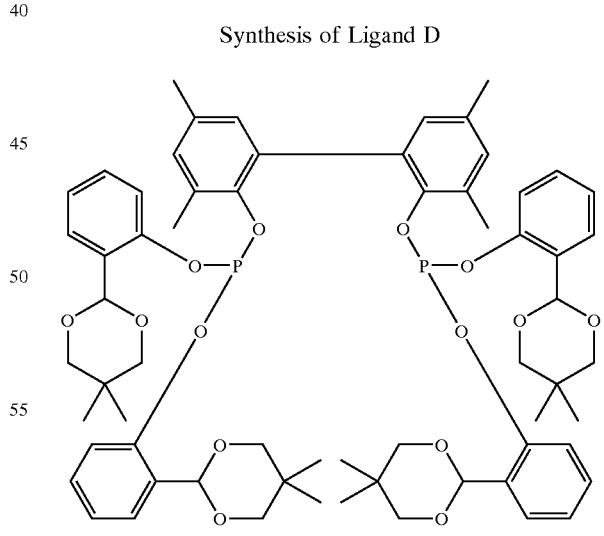

Acetal C (1.67 g, 8.0 mmol) and PCl$_3$ (0.55 g, 4 mmol) were dissolved in toluene (40 mL) and the solution was cooled to 40° C. Et$_3$N (1.0 g, 10.0 mmol) in toluene (15 mL) was added dropwise with stirring. The reaction was allowed to slowly warm to room temperature then stirred overnight. A mixture of Et$_3$N (0.4 g, 4.0 mmol) and 3,3',5,5'- tetramethyl-2,2'-biphenol (0.48 g, 2.0 mmol) in toluene (15 mL) was added to the phosphorochloridite solution, and the mixture was stirred for 2 hours. The solution was filtered through Celite®, and the solvent was evaporated to give 1.3 g of white sticky solid. $^{31}$P NMR ($C_6D_6$): δ 135.2, other peaks at 142.7, 134.5 ppm.

EXAMPLE 13

Synthesis of Ligand E

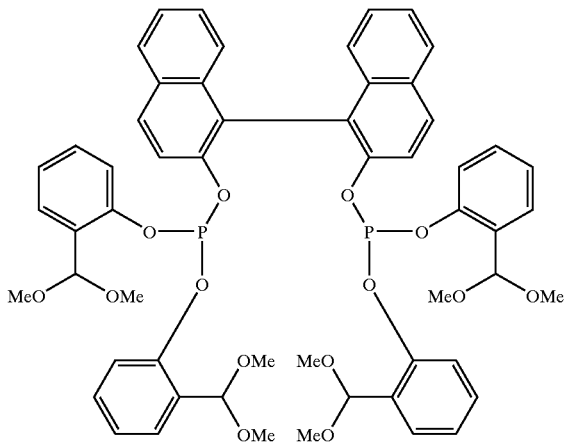

Acetal D (336 mg, 2.0 mmol) and $Et_3N$ (1.0 g, 10.0 mmol) were dissolved in toluene (5 mL) and the solution was added dropwise to a stirred, −20° C. solution of $PCl_3$ (137 mg, 1.0 mmol) in toluene (2 mL). The reaction was stirred for 20 min, and then a mixture of 2,2'-binaphthol (143 mg, 0.5 mmol) and $Et_3N$ (0.4 g, 4.0 mmol) in toluene (3 mL) was added to the phosphorochloridite solution, and the mixture was stirred 1 hour. The solution was filtered and the solvent was evaporated to give 0.57 g of product. $^{31}$P NMR ($C_6D_6$): δ 131.7, minor peaks at 146, 130.1 ppm.

EXAMPLE 14

Synthesis of Ligand F

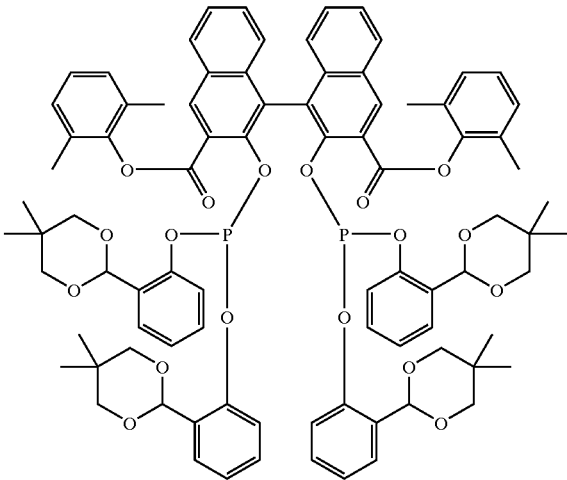

With stirring under a dry, nitrogen atmosphere, a dry ether solution (50 mL) of Acetal C was added dropwise over a 20 minute period to N,N-diethylphosphoramidous dichloride (3.36 gm, 19.3 mmol) and dry triethylamine (4.88 gm, 48.3 mmol) dissolved in 150 mL of dry ether. After stirring overnight, the triethylammonium chloride solids were vacuum filtered and washed with dry ether (3×15 mL). The combined ether filtrates were evaporated to yield the desired phosphoramidite, $[2-[5,5-(CH_3)_2-1,3-C_3H_5O_2]C_6H_4O]_2PN(C_2H_5)_2$, as a white solid (9.33 gm). $^{31}$P NMR ($CDCl_3$): 141.9 ppm.

The phosphoramidite (9.33 gm, 18.0 mmol) was dissolved in dry ether (150 mL) then cooled to −35° C. in a drybox freezer. Hydrogen chloride in dry ether (36 mL, 1.0 M) was added dropwise over a 20 minute period to the cold, stirred phosphoramidite solution. The resulting mixture was returned to the freezer for another 1.5 hours. The solids were vacuum filtered and washed with dry ether (20 mL). The combined ether filtrates were evaporated to yield the phosphorochloridite of acetal C, $[2-[5,5-(CH_3)_2-1,3-C_3H_5O_2]C_6H_4O]_2PCl$. $^{31}$P NMR ($CDCl_3$): 163.9 ppm.

Di(2,6-dimethylphenyl) 2,2'-dihydroxy-1,1'-binaphthalene-3,3'-dicarboxylate (0.792 gm, 1.36 mmol) was added to the phosphorochloridite of acetal C (1.634 gm, 3.40 mmol) dissolved in dry ether (50 mL). After cooling to 35° C. in a drybox freezer, the light yellow mixture was stirred as dry triethylamine (0.344 gm, 3.39 mmol) was added dropwise over a 5 minute period. After stirring at ambient temperature for another 2.5 hours, the mixture was filtered through dry, neutral alumina and the alumina was rinsed with dry tetrahydrofuran (50 mL). The combined filtrates were evaporated to yield the desired diphosphite ligand as a light yellow solid (0.376 gm). $^{31}$P NMR ($CDCl_3$): 129.7 ppm.

EXAMPLE 15

Synthesis of Ligand G

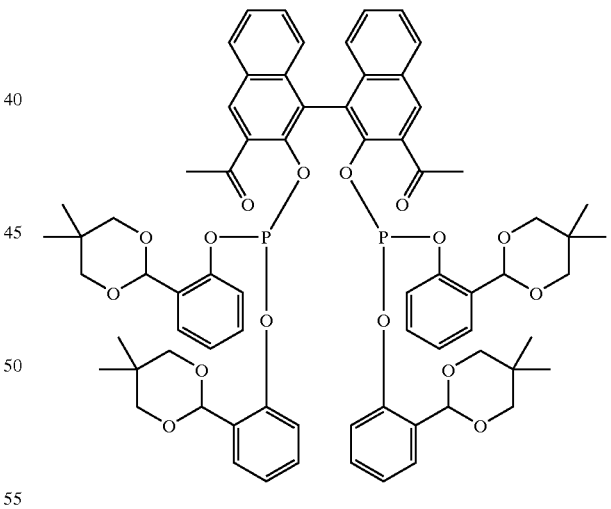

With stirring under dry nitrogen, 2,2'-dihydroxy-1,1'-binaphthalene-3,3'-dicarboxylic acid (1.87 gm, 5.0 mmol) was dissolved in dry tetrahydrofuran (50 mL) then cooled to −78° C. with a dry ice/acetone bath. Methyllithium (25 mL of 1.4M in ether, 35 mmol) was added dropwise then the solution was allowed to warm to ambient temperature. After stirring overnight, the solution was added. slowly to ice cold, 1 M hydrochloric acid (30 mL). The organic phase was washed with water then evaporated. The orange residue was dissolved in dichloromethane and eluted through a silica gel plug. The orange filtrate was evaporated to yield 2,2'- dihydroxy-1,1'-binaphthalene-3,3'-bis(methylketone) as a yellow solid (1.52 gm).

2,2'-Dihydroxy-1,1'-binaphthalene-3,3'-bis(methylketone) (0.200 gm, 0.54 mmol) was added to the phosphorochloridite of Acetal C (0.651 gm, 1.35 mmol) dissolved in dry ether (50 mL). After cooling to −35° C. in a drybox freezer, the light yellow mixture was stirred as dry triethylamine (0.155 gm, 1.53 mmol) was added dropwise over a 5 minute period. After stirring at ambient temperature for another 48 hours, the mixture was filtered through dry, neutral alumina and the alumina was rinsed with dry ether (50 mL). The combined filtrates were evaporated to yield the desired diphosphite ligand as a light yellow solid (0.466 gm). $^{31}$P NMR (CDCl$_3$): 134.1 ppm.

EXAMPLE 16

Synthesis of Ligand H

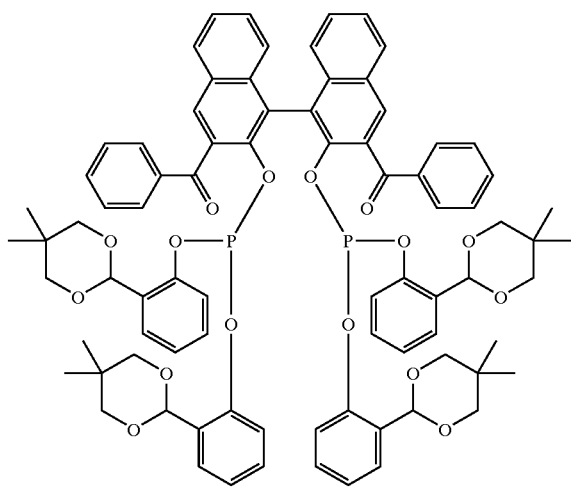

With stirring under dry nitrogen, 2,2'-dihydroxy-1,1'-binaphthalene-3,3'-dicarboxylic acid (8.42 gm, 22.5 mmol) was dissolved in dry tetrahydrofuran (500 mL) then cooled to −78° C. with a dry ice/acetone bath. Phenyllithium (100 mL of 1.8 M in 70/30 cyclohexane/ether, 0.18 mol) was added dropwise then the solution was allowed to warm to ambient temperature. After stirring overnight, deionized water (50 mL) was slowly added to the reaction solution at 0° C. With vigorous stirring, 1 M hydrochloric acid was added dropwise until the water phase became strongly acidic (pH=2). The organic phase was washed with water in a separatory funnel then dried over magnesium sulfate and evaporated. The orange residue was redissolved in dichloromethane and eluted through a silica gel plug. The orange filtrate was evaporated to yield 2,2'-dihydroxy-1,1'-binaphthalene-3,3'-bis(phenylketone) as a yellow solid (10.5 gm).

2,2'-Dihydroxy-1,1'-binaphthalene-3,3'-bis(phenylketone) (0.715 gm, 1.45 mmol) was added to the phosphorochloridite of Acetal C (1.738 gm, 3.62 mmol) dissolved in dry ether (50 mL). After cooling to −35° C. in a drybox freezer, the orange solution was stirred as dry triethylamine (0.365 gm, 3.62 mmol) was added dropwise over a 5 minute period. After stirring at ambient temperature for another 2.5 hours, the yellow mixture was filtered through dry, neutral alumina and the alumina was rinsed with dry ether (50 mL). The combined filtrates were evaporated to yield the desired diphosphite ligand as a light yellow solid (1.68 gm). $^{31}$P NMR (CDCl$_3$): 134.0 ppm.

EXAMPLE 17

Synthesis of Ligand I

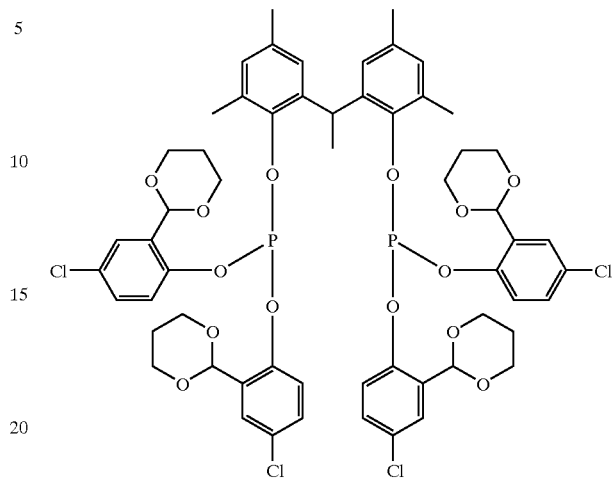

Into a round bottom flask was added 0.412 g of phosphorus trichloride and about 50 mL of toluene. The mixture was cooled to −30° C. and 1.288 g of Acetal G was added. A precooled solution (−30° C.) of triethylamine (0.800 g) in 20 mL of toluene was added dropwise. A $^{31}$P NMR of the mixture indicated a major resonance at 164.1 ppm with minor resonances at 193.3 and 132.5 ppm. To this mixture was added 0.405 g of 2,2'-ethylidenebis(4,6-dimethylphenol), prepared according to Yamada et al., *Bull. Chem. Soc. Jpn.*, 1989, 62, 3603, in 10 mL of toluene and then 0.600 g of triethylamine. The mixture was stirred overnight and then filtered through Celite®, washed with toluene, and solvent removed by rotary evaporation to yield the 1.8 g of a white solid. $^{31}$P{H} (202 MHz, C$_6$D$_6$): major resonance at 134.9 ppm, minor resonances at 132.6, 132.2, 130.9, 128.2 ppm. APCI MS (atmospheric pressure chemical ionization mass spectroscopy): Found: 1183.1; calculated for C$_{58}$H$_{60}$O$_{14}$Cl$_4$P$_2$+H$^+$:1183.22.

EXAMPLE 18

Synthesis of Ligand J

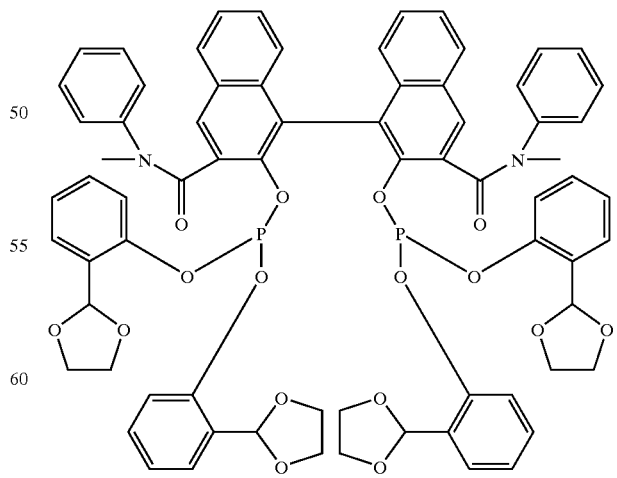

Acetal A (1.33 g, 8 mmol) and PCl$_3$ (0.55 g, 4 mmol) were dissolved in toluene (40 mL) and cooled to −40° C. A solution of Et₃N (1.0 g, 10 mmol) in toluene (15 mL) was added dropwise to the cold solution. The reaction was allowed to warm to room temperature then stirred overnight. A solution of (N-methyl, N-phenyl)-2,2'-dihydroxy-1,1'-binaphthalene-3,3'-dicarboxamide (1.1 g, 2 mmol) and Et₃N (0.4 g, 4 mmol) in toluene (15 mL) was added and the mixture was stirred for 2 hours. The mixture was filtered through Celite®, and the solvent was removed to give 2.3 g of a yellow sticky product. $^{31}$P NMR: δ 131.6, smaller peak at 127.6, broad peaks at 133.1, 144.1 ppm.

EXAMPLE 19

Synthesis of Ligand K

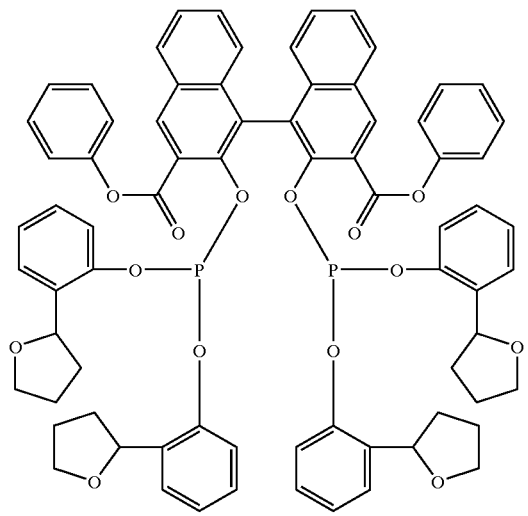

With stirring under a dry, nitrogen atmosphere, 2-(tetrahydro-2-furanyl)phenol (5.10 gm, 31.1 mmol) was added dropwise to N,N-diethylphosphoramidous dichloride (2.702 gm, 15.5 mmol) and dry triethylamine (3.77 gm, 37.3 mmol) dissolved in 200 mL of dry ether. After one hour, the triethylammonium chloride solids were vacuum filtered and washed with dry ether. (3×15 mL). The combined ether filtrates were evaporated to yield the desired phosphoramidite, [2-(2-C₄H₇O)C₆H₄O]₂PN(C₂H₅)₂, as a viscous oil. $^{31}$P NMR (CDCl₃): 142.2, 142.0, 141.5, and 141.2 ppm due to a mixture of stereoisomers.

The phosphoramidite (5.0 gm, 11.6 mmol) was dissolved in dry ether (50 mL) then cooled to −35° C. in a drybox freezer. Hydrogen chloride (24 mL, 1.0 M in dry ether) was added dropwise to the cold, stirred phosphoramidite solution. Five minutes after the addition was complete, the solids were vacuum filtered and washed with dry ether (3×15 mL). The combined ether filtrates were evaporated to yield the phosphorochloridite of 2-(tetrahydro-2-furanyl)phenol, [2-(2-C₄H₇O)C₆H₄O]₂PCl. $^{31}$P NMR (C₆D₆): 163.7, 162.9, 162.5 ppm due to a mixture of stereoisomers.

Diphenyl 2,2'-dihydroxy-1,1'-binaphthalene-3,3'-dicarboxylate (0.425 gm, 0.807 mmol) was added to the phosphorochloridite of 2tetrahydro-2-furanyl)phenol (0.793 gm, 2.02 mmol) dissolved in dry ether (50 mL). After cooling to −35° C. in a drybox freezer, the light yellow mixture was stirred as dry triethylamine (0.204 gm, 2.02 mmol) was added dropwise over a 10 minute period. The mixture was filtered through dry, neutral alumina and the alumina was rinsed with dry ether (3×25 mL). The combined ether filtrates were evaporated to yield the desired diphosphite ligand as a white solid (0.81 gm). $^{31}$P NMR (C₆D₆): several peaks centered at 131 ppm due to a mixture of stereoisomers.

EXAMPLE 20

Synthesis of Ligand L

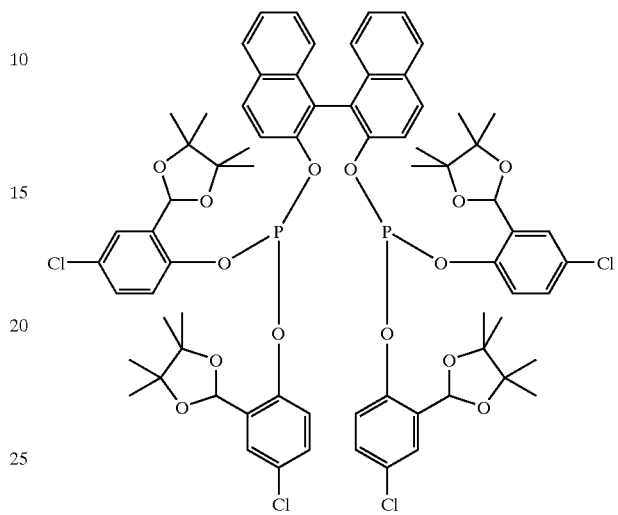

Into a round bottom flask was added 0.343 g of phosphorus trichloride and about 50 mL of toluene. The mixture was cooled to −30° C. and 1.284 g of acetal F was added. A precooled solution (−30° C.) of triethylamine (0.700 g) in 20 mL of toluene was added dropwise. A $^{31}$P NMR analysis of the mixture indicated a major resonance at 162.6 ppm with minor resonances at 190.4 and 130.7 ppm. To this mixture was added 0.358 g of 2,2'-binaphthol in 10 mL of toluene and then 0.600 g of triethylamine. The mixture was stirred overnight and then filtered through Celite®, washed with toluene and solvent removed by rotary evaporation to give 1.753 g of a white solid. $^{31}$P{H} (202 MHz, C₆D₆): major resonance at 130.0 ppm, other resonances at 143.1 and 130.8 ppm. APCI MS: Found: 1366.3; calculated for C₇₂H₇₆O₁₄Cl₄P₂: 1366.346.

EXAMPLE 21

Synthesis of Ligand M

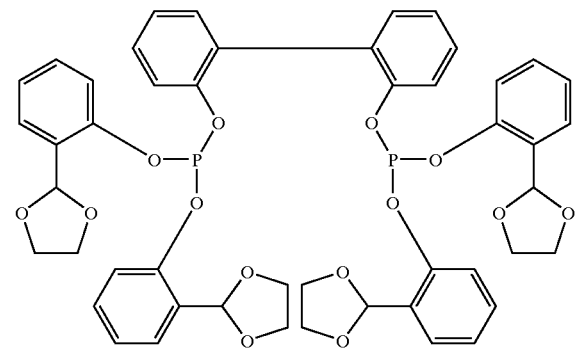

Acetal A (1.33 g, 8 mmol) and PCl₃ (0.55 g, 4 mmol) were dissolved in toluene (40 mL) and cooled to −40° C. A solution of Et₃N (1.0 g, 10 mmol) in toluene (15 mL) was added dropwise to the cold solution. The reaction was allowed to warm to room temperature then stirred overnight. A solution of 2,2'-biphenol (0.37 g, 2 mmol) and Et₃N (0.4 g, 4 mmol) in toluene (15 mL) was added and the mixture was stirred for 2 hours. The mixture was filtered through Celite®, and the solvent was removed to give 1.79 g of a pale, oily residue. ³¹P NMR: δ 131.3, smaller peaks at 132.5, 144.2 ppm,

EXAMPLE 22

Synthesis of Ligand N

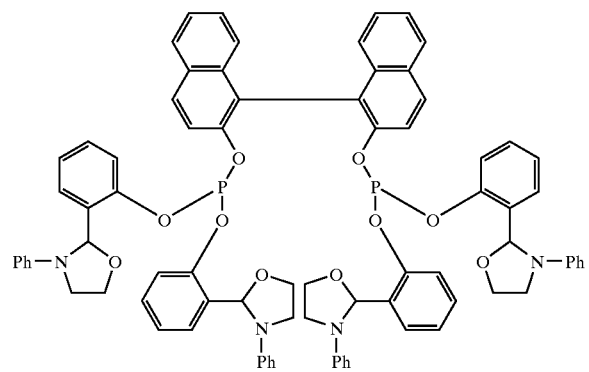

Amino-Acetal E (482 mg, 2.0 mmol) and Et₃N (0.67 g) were dissolved in toluene (10 mL). This solution was added to a −20° C. solution of PCl₃ (137 mg, 1 mmol) in toluene (3 mL) over a 5 minute period. After the addition, the mixture was stirred at −20° C. for 15 minutes. A suspension of 2,2'-binaphthol (143 mg, 0.5 mmol) and Et₃N (0.33 g) in toluene (5 mL) was added in one portion and the mixture was allowed to stir for 2 days. The mixture was filtered, and the solvent was evaporated to give 0.47 g of product ³¹P NMR: δ 132.1, 130.8, small peaks at 147.2, 144.9 ppm.

EXAMPLE 23

Synthesis of Ligand O

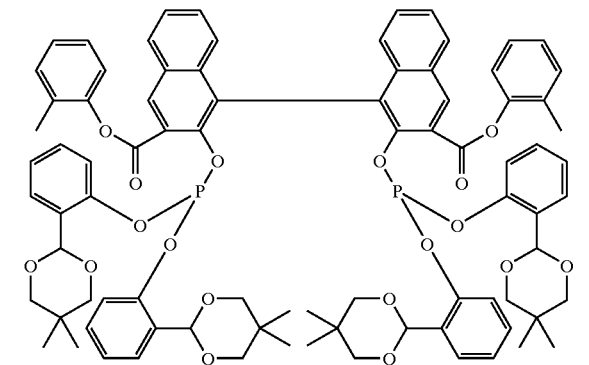

Acetal C (25.0 g, 120 mmol) and PCl₃ (8.23 g, 60 mmol) were dissolved in toluene (100 mL) and cooled to −20° C. Approximately two-thirds of a Et₃N (21.0 g, 200 mmol) solution in toluene (100 mL) was added dropwise to the acetal solution over a 30 minute period. The mixture was stirred for another 15 min at −20° C. Over the next hour, small portions of solid di(2-tolyl)-2,2'-dihydroxy-1,1'-binaphthalene-3,3'-dicarboxylate (16.5 g, 29.8 mmol), were added to the cold, chloridite solution (−10 to −15° C.) while alternating with equivalent portions of the remaining Et₃N solution. The mixture was stirred for an hour, and the mixture was filtered. The solvent volume was reduced to between 100–200 mL toluene, and the solution was allowed to stand for 2 days. A fine white precipitate was collected (20.6 g). ³¹P NMR: δ 129.5 very small peaks at 133.1, 146.7 ppm.

EXAMPLE 24

Preparation of Carbon-supported Catalyst Using Ligand O

Crystalline Rh(CO)₂(acac) (1 equiv), was dissolved into 2–4 mL toluene. The light-yellow solution was added to solid ligand O (100 mg), resulting in some bubbling and a change in solution color.

5 g of granular (40–60 mesh) activated carbon (EM Scientific) was dried and calcined by heating in flowing helium (100 mL/min) at 850° C. for 5 hrs. The dried carbon was transferred to a nitrogen filled glove box where it was slurried into a toluene solution containing rhodium and ligand O. The slurry was stirred for 15 min then evaporated to dryness in vacuum. Residual solids, deposited on the sides of the vessel; were rinsed with extra toluene such that all were eventually deposited only onto the carbon. The dry solid was pumped overnight to remove residual toluene and then capped and stored in the glove box for catalytic testing.

EXAMPLE 25

Synthesis of Ligand P

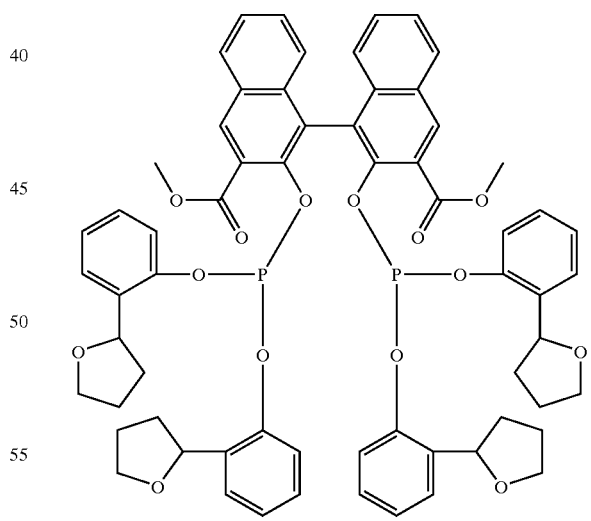

This diphosphite was prepared according to the general procedure described for ligand K except substituting the corresponding dimethyl ester for diphenyl 2,2'-dihydroxy-1,1'-binaphthalene-3,3'-dicarboxylate. The product was an oil. ³¹P NMR (C₆D₆): 131.0, 130.9, 130.8, 1306, 130.4, 130.3 ppm due to a mixture of stereoisomers along with cyclic monophosphite impurity at 146.8 and 146.4 ppm.

EXAMPLE 26

Ligand Q - Synthesis of Polymer Supported Ligand

Preparation of a Supported Disubstitued Binaphthol

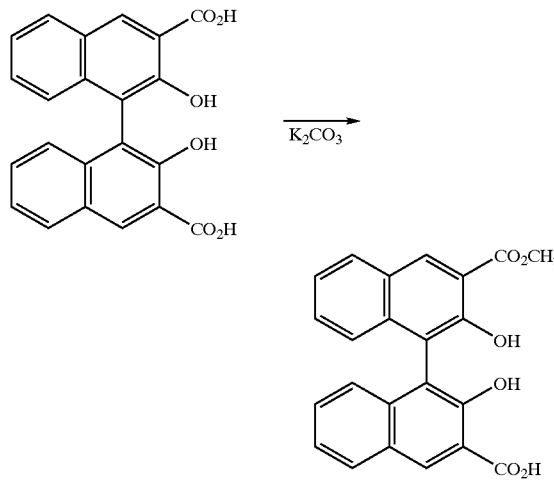

A mixture of 50 g (60 mmol) of Merrifield resin (polCH$_2$Cl where pol=1–2% crosslinked polystyrene, 200–400 mesh beads), 2,2'-dihydroxy-1,1'-binaphthalene-3,3'-dicarboxylic acid (33.7 g), potassium carbonate (12.4 g) and DMF (dimethlyformamide) (350 ml) was heated at 90° C. with stirring for 8 hrs. The color of the resin changed from white to green-yellow. The mixture was diluted with water, filtered, washed with H$_2$O, DMF, and acetone, and then thoroughly dried in the air to give the desired product. IR (KBr, cm$^{-1}$): 1712 (vs), 1676 (vs).

Functionalization of the Carboxylate Group

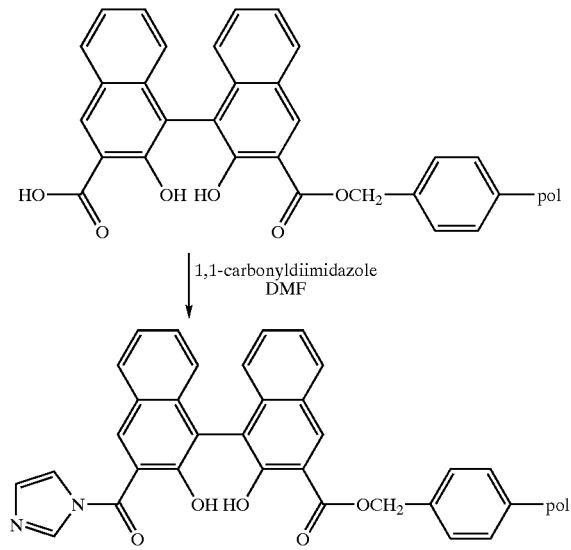

25 g (18.7 mmol) of the polymer supported diol was suspended in 150 mL of anhydrous DMF, and to this mixture was added 4.54 g (28 mmol) of 1,1-carbonyldiimidazole. The mixture was shaken overnight, and the polymer beads turned deep red-orange. The beads were collected by filtration and washed with DMF (3×100 mL), toluene (3×100 mL), and CH$_2$Cl$_2$ (3×100 mL) before drying under vacuum. IR (cm$^{-1}$, KBr): 1771 (vs), 1720 (vs).

Esterification of the Side Chain

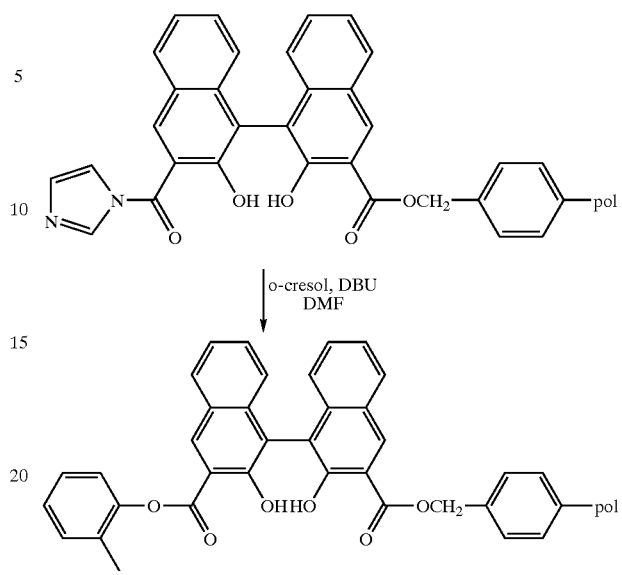

25.93 g (18.7 mmol) of the polymer supported imidazolyl ester was suspended in 150 mL of anhydrous DMF. 10.10 g (93.5 mmol) of ortho-cresol and 2.845 g (18.7 mmol) of DBU (1,8-Diazabicyclo[5.4.0]undec-7-ene) were added. The mixture was shaken for two days at room temperature. The product was collected by filtration and washed with DMF, toluene, and CH$_2$Cl$_2$ (3×100 mL) before final vacuum drying. IR (cm$^{-1}$, KBr): 1759 (w), 1720 (w), 1675 (vs).

Synthesis of Ligand Q

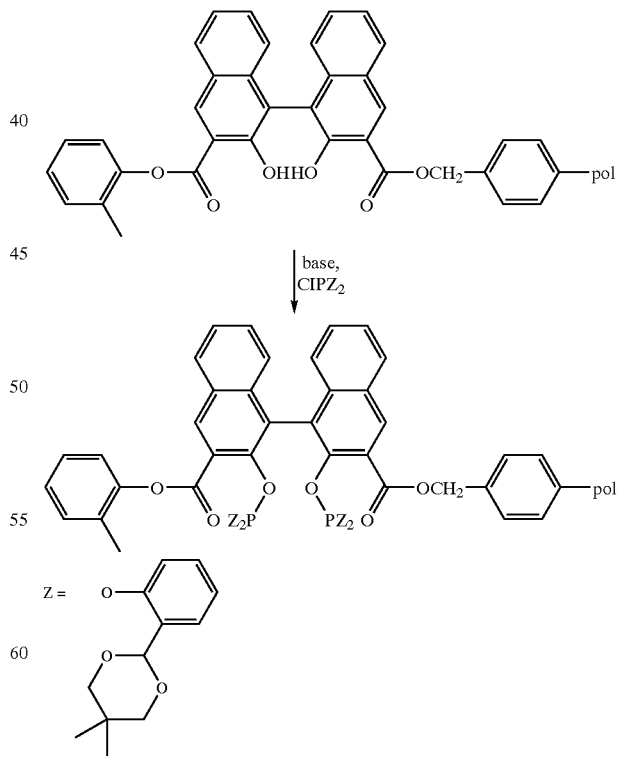

24.8 g (17.4 mmol) of the supported diol was suspended in 150 mL of toluene, and to this suspension was added 25.0 g (52.1 mmol) of the phosphorochloridite derived from acetal C and 13.4 g of diisopropylethylamine. The mixture was shaken overnight at room temperature. The pale yellow beads were collected by filtration, washed with toluene, $CH_2Cl_2$ (3×100 mL), and then dried under vacuum. Elemental analysis: 1.15 wt % P (average).

EXAMPLE 27

Synthesis of Ligand R

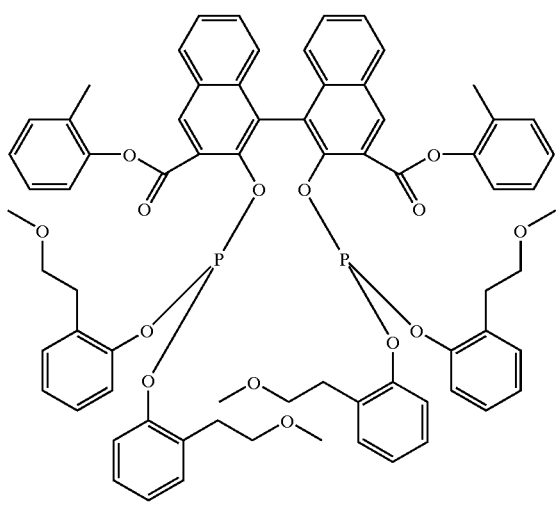

2-Hydroxyphenethyl alcohol was reacted with bromoacetonitrile in the presence of potassium carbonate to protect the phenolic oxygen, as in *Tetrahedron Letters*, 1993, 34, 7567–7568: 2-Hydroxyphenethyl alcohol was dissolved in 20 mL acetone. To this was added 1.2 g potassium carbonate. To the stirring mixture was added 0.87 g bromoacetonitrile under nitrogen. The mixture was 5, stirred overnight. The mixture was filtered, and the filtrate was concentrated. The product was purified by flash column chromatography on silica gel, eluting with 1/1 ethyl acetate:hexanes, to yield 81% of 2-(o-cyanomethyl)phenethyl alcohol. $^1$H NMR ($CD_2Cl_2$): 2.81 (t, 2H), 3.72 (t, 2H), 4.77 (s, 2H), 6.92 (dd, 2H), 7.18 (d, 2H). 2-(o-Cyanomethyl)phenethyl alcohol (1:0 g, 6.3 mmol) was dissolved in 5 mL anhydrous DMF and added to a stirring solution of sodium hydride (0.25 g, 10.4 mmol) in DMF (20 mL). After hydrogen evolution ceases, methyl iodide (0.47 mL, 7.5 mmol) was added dropwise. The mixture was stirred at room temperature under nitrogen for five hours. After aqueous workup, the product was purified using flash column chromatography on silica gel, eluting with 1/5 ethyl acetate/hexanes solvent mixture to yield 0.56 g (56%) of the desired product, 2-(o-cyanomethyl)phenethyl methyl ether. $^1$H NMR ($CD_2Cl_2$): 2.96 (t, 2H), 3.36 (s, 3H), 3.60 (t, 2H), 4.86 (s, 2H), 7.04 (dd, 2H), 7.31 (d, 2H).

2-(o-Cyanomethyl)phenethyl methyl ether was deprotected following the procedure described in *Tetrahedron Letters*, 1993, 34, 7567–7568. 2-(o-Cyanomethyl)phenethyl methyl (0.56 g, 3.13 mmol) was dissolved in 40 mL anhydrous ethanol. Platinum dioxide (20 mg) was added to this solution. The solution was purged with hydrogen for 10 minutes, and then stirred under hydrogen overnight. The mixture was filtered, and the filtrate was concentrated. The residue was redissolved in ether, washed with water, and dried over $MgSO_4$. After concentration, 0.39 g (82%) of 2-hydroxyphenethyl methyl ether was isolated. $^1$H NMR ($CD_2Cl_2$): 2.78 (t, 2H), 3.32 (s, 3H), 3.60 (t, 2H), 2-Hydroxyphenthyl methyl ether was reacted with diethylphosphoramidous dichloride to yield the corresponding phosphorous. amidite in the same manner as described for Example 25. $^{31}$P NMR (toluene): 137 ppm. The phosphoroamidite was treated with 1M HCl solution following the procedure described for Example 25 to yield the corresponding phosphorochloridite. $^{31}$P NMR (toluene): 165 ppm. The phosphochloridite was then reacted with di(2-tolyl)-2,2'-dihydroxy-1,1'-binaphthalene-3,3'-dicarboxylate in the same manner as described for Example 19. $^{31}$P NMR (toluene): 125 (major), 127 (minor), 142 (minor).

EXAMPLE 28

Synthesis of Ligand S

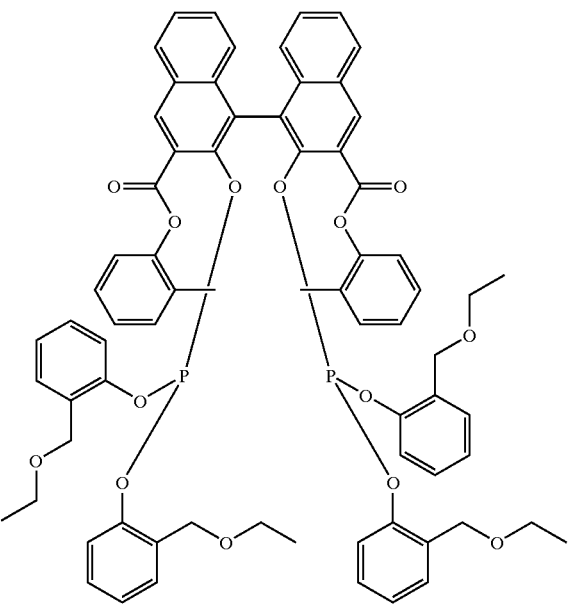

The ethyl ether of 2-hydroxybenzyl alcohol was prepared according to a literature procedure reported in *Recueil. Trav. Chim. Pays-Bas* 1955, 74, 1448. The phosphorochloridite of this phenol was prepared from $PCl_3$ in toluene with triethylamine as base at –30° C. $^{31}$P nmr of the reaction mixture: 158, 125 ppm. To the phosphorochloridite solution was added di(2-tolyl)-2,2'-dihydroxy-1,1'-binaphthalene-3,3'-dicarboxylate in the presence of triethylamine, as described in example 27. $^{31}$P NMR (toluene): 131 (major), 146 (minor) 163 (minor).

EXAMPLE 29

Synthesis of Ligand T

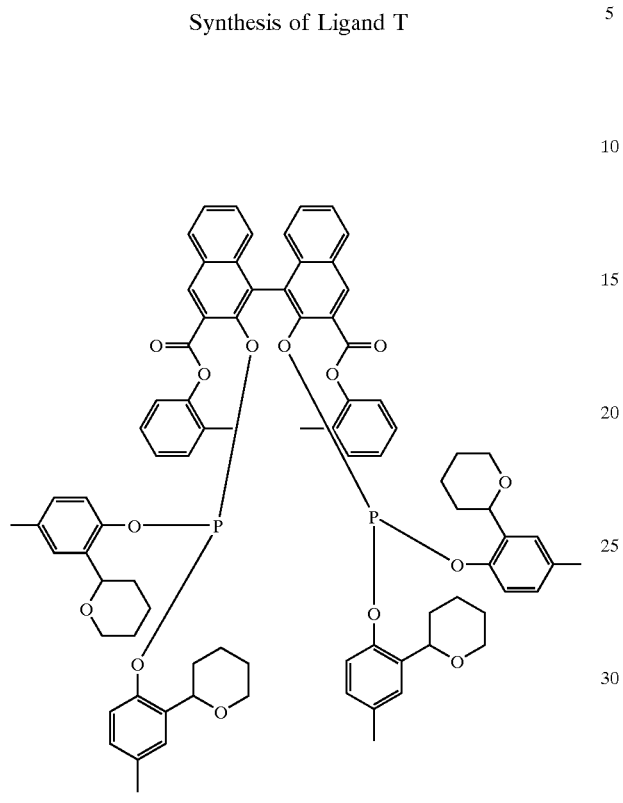

2-(2-Tetrahydropyranyl)-4-methyl-phenol was prepared from the corresponding phenol following the procedure outlined in *Aust. J. Chem.*, 1988, 41, 69–84. In a nitrogen purged glove box, 2-(2-tetrahydropyranyl)-4-methyl-phenol (0.96 g, 5.0 mmol) was dissolved in 25 ml diethyl ether, and cooled to −40° C. Diethylphosphoramidous dichloride (2.5 mmol) was added, followed by triethylamine (6 mmol). The reaction mixture was stirred at room temperature for one hour, then filtered over a pad of Celite®. The filtrate was concentrated in vacuo to yield 1.1 g (90%) of the corresponding phosphorous amidite. $^{31}$P NMR(toluene): 142.7, 142.6. The above phosphorous amidite (1.1 g) was dissolved in 25 mL anhydrous ether and cooled to −40° C. To the stirring phosphoramidite solution was slowly added 4.4 mL of precooled 1M HCl solution in ether. Upon addition, white precipitate formed. The mixture was stirred for 10 minutes, and cooled back to −40° C. for 2 hours. The resulting slurry was filtered over a pad of Celite®, and concentrated in vacuo to yield 0.92 g of the corresponding phosphorochloridite. $^{31}$P NMR (toluene): 161.6 ppm. The above phosphorochloridite was reacted with di(2-tolyl)-2,2'-dihydroxy-1,1'-binaphthalene-3,3'-dicarboxylate and triethylamine to yield the corresponding ligand. $^{31}$P NMR(toluene): 130 (major).

EXAMPLE 30

Synthesis of Ligand U

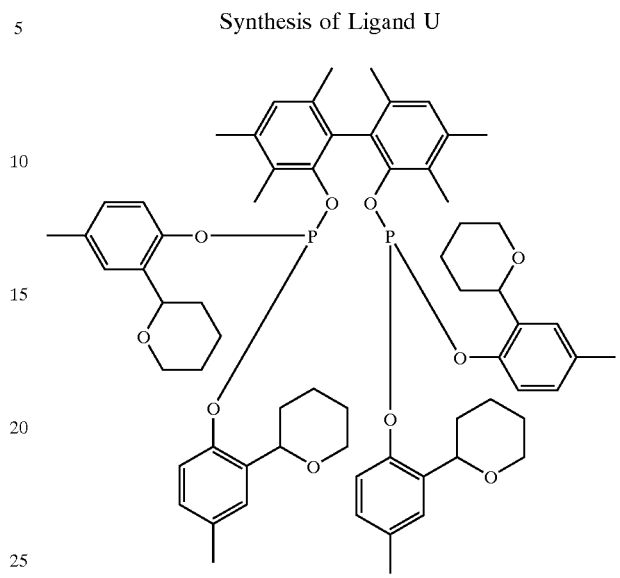

The phosphorochloridite of 2-(2-tetrahydropyranyl)-4-methyl-phenol was prepared as described in example 32. The above phosphorochloridite was reacted with 3,3',4,4',6,6'-hexamethyl-2,2'-biphenol and triethylamine to yield the corresponding ligand. $^{31}$P NMR (toluene): 134, 131, 127.

EXAMPLE 31

Synthesis of Ligand V

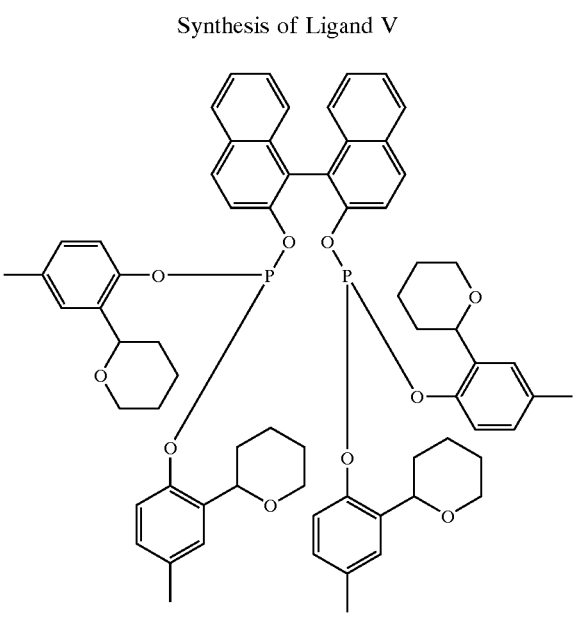

2-(2-Tetrahydropyranyl)-4-methyl-phenol was prepared from the corresponding phenol following the procedure outlined in *Aust. J. Chem.*, 1988, 41, 69–84. In a nitrogen purged glove box, 2-(2-tetrahydropyranyl)-4-methyl-phenol (0.96 g, 5.0 mmol) was dissolved in 25 ml diethyl ether, and cooled to −40° C. Diethylphosphoramidous dichloride (2.5 mmol) was added, followed by triethylamine (6 mmol). The reaction mixture was stirred at room temperature for one hour, then filtered over a pad of Celite®. The filtrate was concentrated in vacuo to yield 1.1 g (90%) of the corresponding phosphorous amidite. $^{31}$P NMR(toluene): 142.7, 142.6. The above phosphorous amidite (1.1 g) was dissolved in 25 mL anhydrous ether and cooled to −40° C. To the stirring phosphorous amidite solution was slowly added 4.4 mL of precooled 1M HCl solution in ether. Upon addition, a white precipitate formed. The mixture was stirred for 10 minutes, and cooled to 40° C. for 2 hours. The resulting slurry was filtered over a pad of Celite®, and concentrated in vacuo to yield 0.92 g of the corresponding phosphorochloridite. $^{31}$P NMR (toluene): 161.6 ppm. The above phosphorochloridite was reacted with 1,1'-bi-2-napthol and triethylamine to yield the corresponding ligand. $^{31}$P NMR (toluene): 131.11, 131.14 (stereoisomers).

EXAMPLE 32

Synthesis of Ligand W

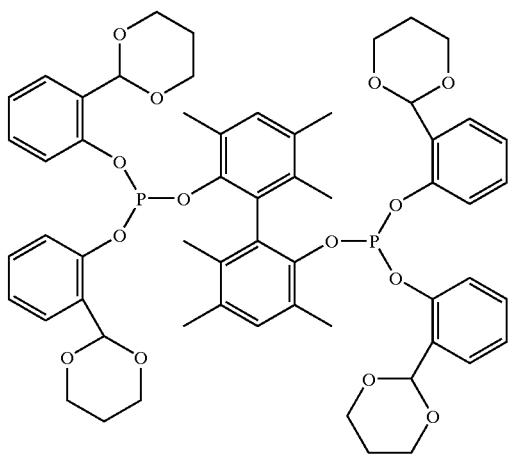

A 100 mL flask was charged with PCl$_3$ (0.412 g) and 50 mL of toluene. The mixture was cooled to −30° C. and the acetal B (1.081 g) was added. This was followed by 0.65 g of NEt$_3$ in 20 mL toluene (precooled to −30° C.), which was added dropwise. After warming to room temperature and stirring for about 40 minutes, the mixture was cooled to −30° C. and 3,3',5,5',6,6'-hexamethyl-2,2'-biphenol (0.406 g) was added, followed 0.6 g of NEt$_3$. The mixture was stirred overnight, filtered through Celite® and the solvent was removed by rotary evaporation. A white solid (1.652 g) was obtained. $^{31}$P NMR in CDCl$_3$: major resonance at 134.42 ppm with minor resonances at 135.08 and 132.6 ppm.

EXAMPLE 33

Synthesis of Ligand X

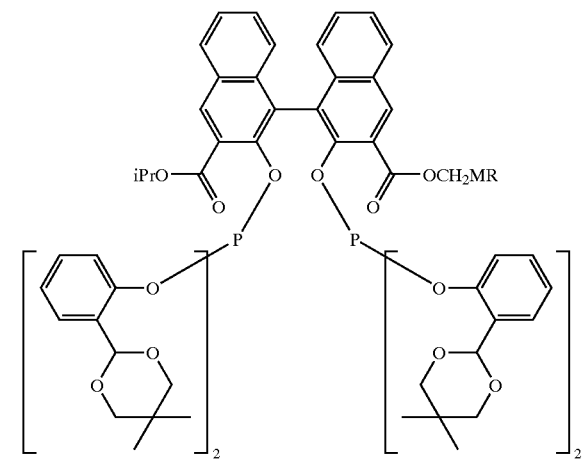

MR = Merrifield resin

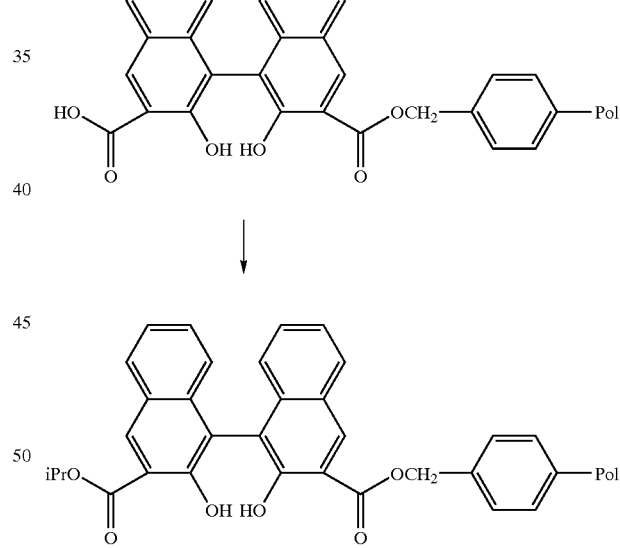

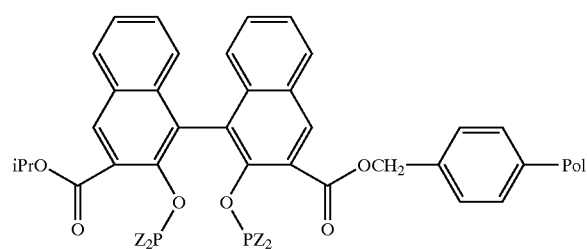

Z =

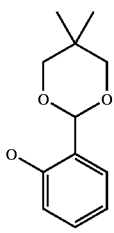

A mixture of 50 g (60 mmol) of Merrifield resin (pol= 1–2% crosslinked polystyrene, 200–400 mesh beads) 2,2'-dihydroxy-1,1'-binaphthalene-3,3'-dicarboxylic acid (33.7 g), potassium carbonate (12.4 g) and DMF (dimethylformamide) (350 ml) was heated at 90° C. with stirring for 8 hrs. The color of the resin changed from white to green-yellow. The mixture was diluted with water, filtered, washed with H$_2$O, DMF, and acetone, and then thoroughly dried in air to give the desired product. IR (KBr, cm$^{-1}$): 1712 (vs), 1676 (vs).

81.64 g (84 mmol) of the light yellow polymer supported carboxylic acid/ester was suspended in 300 mL of anhydrous DMF containing 13.6 g (84 mmol) of carbonyldiimidazole. After stirring at room temperature overnight, the orange intermediate was isolated by filtration and washed with DMF (3×). The polymer was then placed in a mixture of DMF (200 mL) and iPrOH (51.4 mL, 672 mmol) and the mixture was stirred overnight at room temperature. The polymer supported diol/diester product was then isolated by filtration and washed with THF and acetone before air drying.

1.7 g (1.0 mmol) of the polymer supported diol of the previous example was suspended in 15 mL of toluene, and to this was added 1.7 mL (10 mmol) of diisopropylethylamine and 4.0 mmol of the appropriate phosphorochloridite. The suspension was shaken at room temperature overnight. The colorless product was then filtered, washed with toluene (3×10 mL), DMF (3×10 mL), and CH$_2$Cl$_2$ (methylene chloride) (3×10 mL) before drying under vacuum.

Elemental analysis: 1.45% P.

A sample of the polymer supported bis(phosphite) was treated with Ni(COD)$_2$ to give the brown-orange Ni(COD) loaded derivative. This material was then treated with CO at 1 atm and room temperature to give the light yellow polymer supported P$_2$Ni(CO)$_2$ complex, characterized by its infrared spectrum in KBr: 2051.7 (vs), 2001.3 (vs) cm$^{-1}$.

EXAMPLE 34

Synthesis of Ligand Y

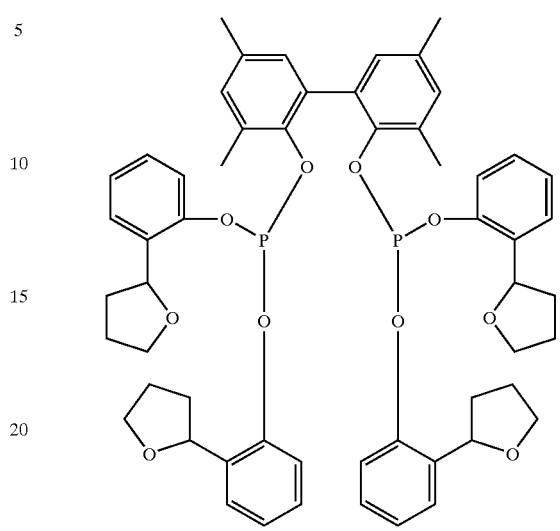

3,3',5,5'-Tetaamethyl-2,2'-dihydroxy-1,1'-biphenylene (0.303 gm, 1.25 mmol) was added to a toluene solution (50 mL) of triethylamine (0.41 gm, 4.0 mmol) and the phosphorochloridite (1.11 gm, 2.8 mmol) of 2-(tetrahydrofuran-2-yl)phenol. After stirring overnight, the solids were vacuum filtered and washed with toluene (3×5 mL). The filtrate was evaporated to yield the product. $^{31}$P NMR (CDCl$_3$, 202 MHz): several peaks between 134.9 and 133.6, and several peaks between 131.2 and 127.5 ppm.

EXAMPLE 35

Synthesis of Ligand Z

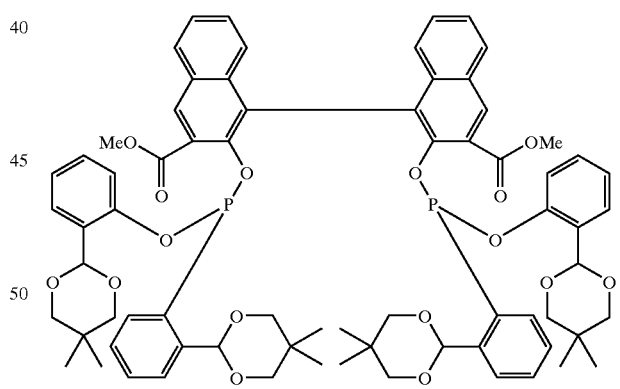

Acetal C (1.67 g, 8.0 mmol) and PCl$_3$ (0.55 g, 4 mmol) were dissolved in toluene (40 mL) and the solution was cooled to −40° C. Et$_3$N (1.0 g, 10.0 mmol) in toluene (15 mL) was added dropwise with stirring. The reaction was allowed to slowly warm to room temperature then stirred overnight. A mixture of Et$_3$N (0.4 g, 4.0 mmol) and dimethyl 2,2'-dihydroxy-1,1'-binaphthalene-3,3'-dicarboxylate (0.8 g, 2.0 mmol) in toluene (15 mL) was added to the phosphorochloridite solution, and the mixture was stirred for 2 hours. The solution was filtered through Celite®, and the solvent was removed to give 2.6 g of product $^{31}$P NMR (C$_6$D$_6$): 132.7, 130.4, 129.7, 129.1 ppm.

EXAMPLE 36

Synthesis of Ligand AA

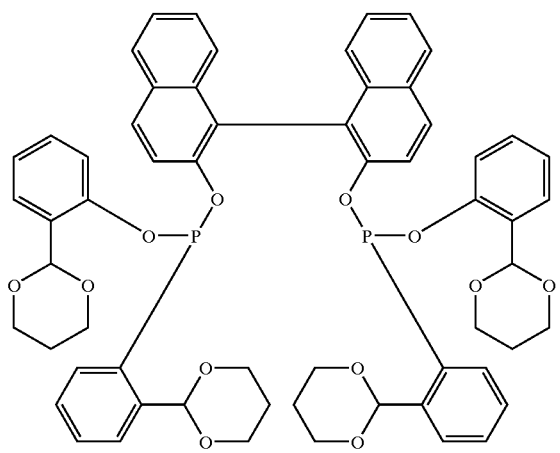

Acetal B (1.44 g, 8.0 mmol) and PCl$_3$ (0.55 g, 4 mmol) were dissolved in, toluene (40 mL) and the solution was cooled to −40° C. Et$_3$N (1.0 g, 10.0 mmol) in toluene (15 mL) was added dropwise with stirring. The reaction was allowed to slowly warm to room temperature then stirred overnight. A mixture of Et$_3$N (0.4 g, 4.0 mmol) and 2,2'-binaphthol (0.57 g, 2.0 mmol) in toluene (15 mL) was added to the phosphorochloridite solution, and the mixture was stirred for 2 hours. The solution was filtered through Celite®, and the solvent was removed to give 1.7 g of product. $^{31}$P NMR (C$_6$D$_6$): 132.4, 134.5, 146.0 ppm.

EXAMPLE 37

Synthesis of Ligand BB

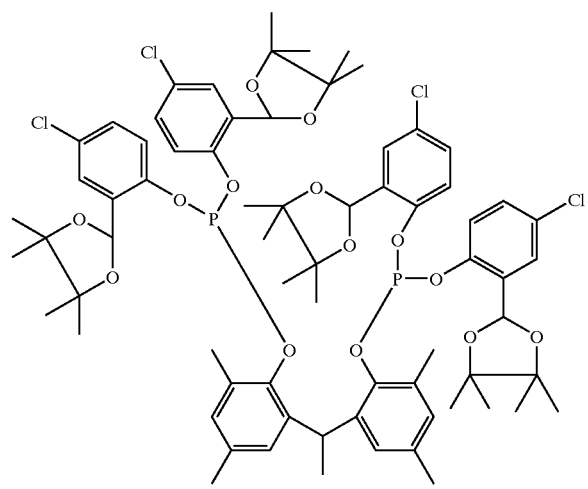

A 100 mL flask was charged with PCl$_3$ (0.343 g) and 50 mL of toluene. The mixture was cooled to −30° C. and acetal F (1.284 g) was added, followed by 7 g of NEt$_3$ in 20 mL toluene (precooled to −30° C.), which was added dropwise. After warming to room temperature and stirring for about 40 minutes, the mixture was cooled to −30° C. and 2,2'-ethylidenebis(4,6-dimethylphenol) (0.338 g) was added and then 0.6 g of NEt$_3$ was added. The mixture was stirred overnight, filtered through Celite® and the solvent was removed by rotary evaporation. A white solid (1.67 g) was obtained. $^{31}$P NMR in C$_6$D$_6$: major peak at 133.104 ppm along with resonances at 130.96, 130.78, 130.01 due to impurities.

EXAMPLE 38

Synthesis of Ligand CC

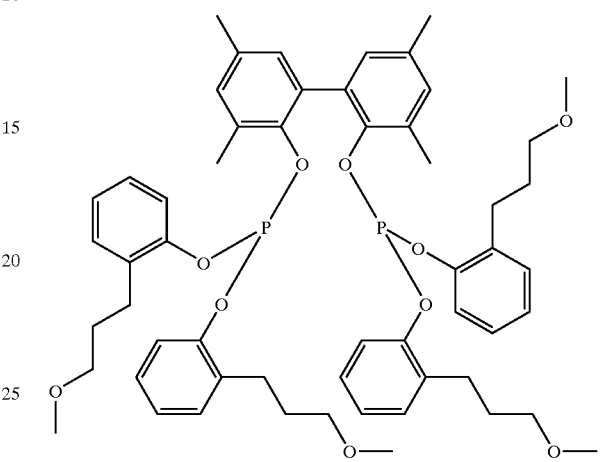

3-(2-Hydroxyphenyl)propan-1-ol was prepared from dihydrocoumarin following the procedure outlined in *J. Chem. Soc.*, 1956, 2455. The phenolic hydroxyl group was protected with cyanomethyl group by the reaction of 3-(2-hydroxyphenyl)propan-1-ol with bromoacetonitrile in the presence of potassium carbonate as described in *Tetrahedron Letters*, 1993, 34, 7567–7568. 3-(2-Hydroxyphenyl)propan-1-ol (27.4 g) was dissolved in 300 mL acetone. To this was added 30 g potassium carbonate, followed by bromoacetonitrile (21.7 g), and the mixture was stirred overnight. The reaction mixture was filtered, concentrated, and purified by flash column chromatography to yield 65% of 3-(2-o-cyanomethylphenyl)propan-1-ol. $^1$H NMR (CDCl$_3$): 1.85 (q, 2H), 2.73 (t, 2H), 3.67 (t, 2H), 4.79 (s, 2H), 6.93 (d, 1H), 7.03 (t, 1H), 7.22 (m, 2H), (t,2H), 3.72 (t, 2H), 4.77 (s, 2H), 6.92 (dd, 2H), 7.18 (d, 2H). 3-(2-o-Cyanomethylphenyl) propan-1-ol (3.0 g) was added to a stirred suspension of potassium hydroxide (3.5 g) in DMSO (dimethylsulfoxide) (30 mL), immediately followed by methyl iodide (4.5 g). The solution was stirred at room temperature for 1.5 hours, then poured into water, and extracted with dichloromethane. The organic layers were combined, washed with water, dried over magnesium sulfate, concentrated, and purified by flash column chromatography on silica gel to yield 1.7 g (53%) of 3-(2-o-cyanomethylphenyl)propyl-1-methyl ether. The cyanomethyl group was cleaved as described in *Tetrahedron Letters*, 1993, 34, 7567–7568. 3-(2-o-Cyanomethylphenyl) propyl-1-methyl ether: (0.77 g, 3.8 mmol) was dissolved in 15 mL anhydrous ethanol in a Fisher-Porter tube. To this solution was added 20 mg platinum dioxide, and the reaction was stirred at room temperature under 35 psi of hydrogen for 2 hours. The mixture was filtered, and the filtrate was concentrated to yield 0.62 g of 3-(2-hydroxyphenyl)propyl-1-methyl ether. $^1$H NMR (CDCl$_3$): 1.41 (q, 2H), 2.72 (t, 2H), 3.37 (t, 2H), 3.40 (s, 3H), 6.85 (m, 2H), 7.09 (m, 2H).

In a nitrogen purged glove box, 3-(2-hydroxyphenyl) propyl-1-methyl ether (1.25 g), was dissolved in 38 ml diethyl ether, and cooled to −40° C. Diethylphosphoramidous dichloride (0.65 g) was added, followed by triethylamine (0.99 g). The reaction mixture was stirred at room temperature for one hour, then filtered over a pad of Celite®. The filtrate was concentrated in vacuo to yield 1.6 g (99%) of the corresponding phosphorous amidite. $^{31}$P NMR (toluene): 136.7. The above phosphorous amidite (1.6 g) was dissolved in 37 mL anhydrous ether and cooled to −40° C. To the stirring amidite solution was slowly added 7.4 mL of precooled 1 M HCl solution in ether. Upon addition, white precipitate formed. The mixture was stirred for 10 minutes, and cooled back to −40° C. for 2 hours. The resulting slurry was filtered over a pad of Celite®, and concentrated in vacuo to yield 1.345 g of the corresponding phosphorochloridite. $^{31}$P NMR (toluene): 161.6 ppm. The above phosphorochloridite was reacted with 3,3',5,5'-tetramethyl-1,1'-biphenol and triethylamine to yield Ligand HH. $^{31}$P NMR (toluene): 134, 142 ppm.

EXAMPLE 39

Synthesis of Ligand DD

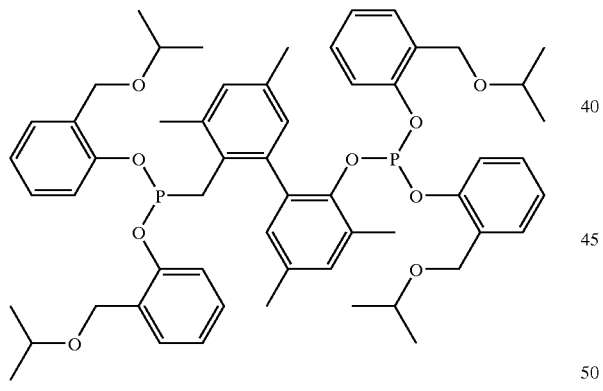

The isopropyl ether of 2-hydroxybenzyl alcohol was prepared according to a literature procedure: *Recueil. Trav. Chim. Pays-Bas*, 1955, 74, 1448. The phosphorochloridite of this phenol (0.499 g) was prepared by the reaction of PCl$_3$ (0.206 g) in toluene (11 g) with triethylamine (0.400 g) at −30° C. This phosphorochloridite was then reacted with 3,3',5,5'-tetramethyl-2,2'-biphenol (0.203 g) and triethyl amine (0.300 g). The mixture was filtered through Celite® and solvent removed by rotary evaporation to give 0.782 g of thick viscous oil. $^{31}$P NMR (CDCl$_3$): major resonance at 133.95 with minor resonances at 142.75 and 130.89 ppm.

EXAMPLE 40

Synthesis of Ligand EE

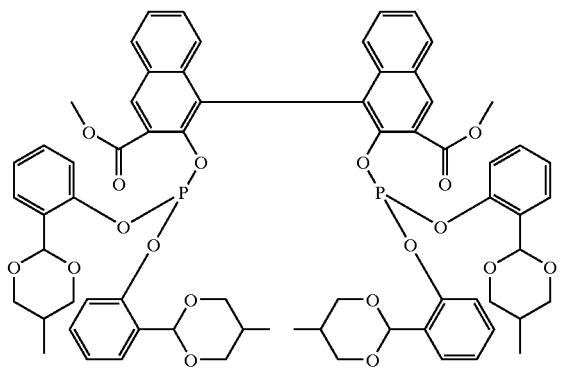

Acetal H (1.55 g, 8.0 mmol) and PCl$_3$ (0.55 g, 4 mmol) were dissolved in toluene (40 mL) and the solution was cooled to 40° C. Et$_3$N (1.0 g, 10.0 mmol) in toluene (15 mL) was added dropwise with stirring. The reaction was allowed to slowly warm to room temperature then stirred overnight. A mixture of Et$_3$N (0.5 g, 5.0 mmol) and dimethyl 2,2'-dihydroxy-1,1'-binaphthalene-3,3'-dicarboxylate (0.8 g, 2.0 mmol) in toluene (15 mL) was added to the phosphorochloridite solution, and the mixture was stirred for 2 hours. The solution was filtered through Celite®, and the solvent was removed to give 2.0 g of product. $^{31}$P NMR (C$_6$D$_6$): δ 131.1, 134.4, 147.4 ppm.

EXAMPLE 41

Synthesis of Ligand FF

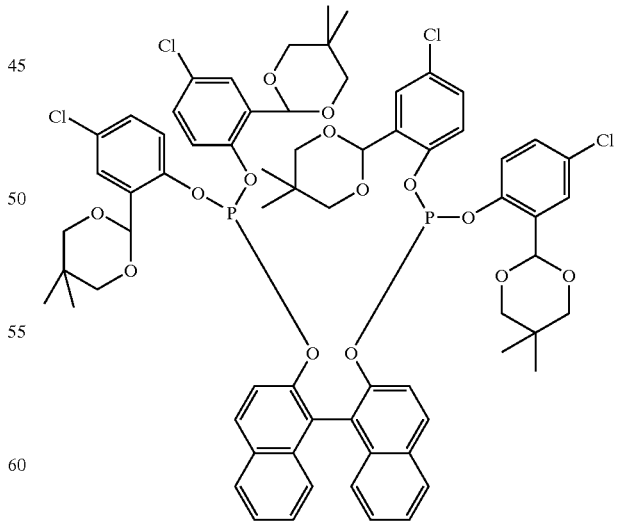

In a 100 mL flask with a magnetic stir bar was charged with 0.412 g of PCl$_3$ and 50 mL of toluene. The mixture was cooled in to −30° C. and the acetal derived from 5-chlorosalicylaldehyde and neopentyl glycol (1.456 g) was added. To this mixture was added dropwise a precooled solution (−30° C.) of triethylamine (0.800 g) in 20 mL of toluene. $^{31}$P NMR of the reaction mixture showed a major resonance at 164.44 ppm along with minor resonances at 193.04 and 131.99 ppm. The mixture was cooled to −30° C., binaphthol (0.429 g) in 10 mL toluene was added and then 0.600 g of triethylamine. The mixture was stirred overnight, filtered through Celite®, washed with toluene and solvent removed by rotary evaporation to give 2.105 g of a white solid. $^{31}$P NMR in $C_6D_6$: major resonance at 131.21 ppm with minor resonances at 144.96 and 132.20 ppm.

EXAMPLE 42

Synthesis of Ligand GG

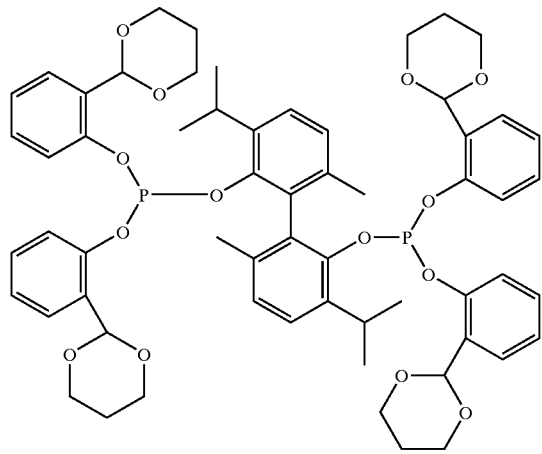

In a 100 mL flask with a magnetic stirrer was charged with 0.412 g of $PCl_3$, 1.081 g of the acetal B, and 20 mL of THF. The solution was cooled to −30° C. and a precooled (−30° C.) solution of triethylamine (0.68 g) in 20 mL of toluene was added dropwise. The slurry was stirred at room temperature for about 1 hour. The slurry was cooled to −30° C., 0.448 g of 3,3'-diisopropyl-6,6'-dimethyl-2,2'-dihydroxy-1,1'-biphenyl was added. To this mixture was added 0.600 g of triethylamine. The mixture was stirred overnight, filtered, solvent removed by rotary evaporation to give 1.668 g of a white solid. $^{31}$P NMR (CDCl$_3$): major resonance at 132.26 ppm with minor resonances at 132.97, 132.86, 135.83, 132.62, 131.76, 128.88 ppm.

EXAMPLES 43–53

Catalyst solutions were prepared by mixing 0.042 mmol of one of the bidentate ligands of the invention and 0.014 mmol of Ni(COD)$_2$ in 457 mg toluene.

BD Hydrocyanation: 74 μL of the Ni catalyst solution (0.0018 mmol Ni) prepared as described above was added to a 4-mL septum-sealed screw-capped vial and cooled to −20° C. After cooling, 120 μL of a solution of HCN in valeronitrile (0.83 mmol HCN) and 280 μL of a solution of BD in toluene (0.925 mmol BD) were added. The vials were sealed and heated at 80° C. Samples were removed after 1.5 and 3 hours. The reaction mixtures were then diluted in diethyl ether (Et$_2$O) and analyzed by GC against valeronitrile as an internal standard.

2M3 Isomerization: 130 μL of a cold solution containing 2M3 and valeronitrile (0.930 mmol 2M3) and 82 μL of a Ni catalyst solution (0.002 mmol Ni) prepared as described above were added to a septum capped vial. The vial was sealed and heated at 125° C. Samples were removed after 1.5 and 3.0 hrs, cooled and diluted in ethylether. The product distribution was analyzed by GC, using valeronitrile as an internal standard.

| Example | Ligand | BD conv. after 3 h (%) | Ratio of 3PN/2M3 from BD | Ratio of 3PN/2M3 isom after 3 h (% conversion to 3PN) |
|---|---|---|---|---|
| 43 | W | 74.2 | 24.7 | 21.5 |
| 44 | B | 64.1 | 1.4 | 16.8 |
| 45 | X | 11.9 | 37.8 | 20.4 |
| 46 | Y | 78 | 1 | 15.4 |
| 47 | U | 89.4 | 0.7 | 15.9 |
| 48 | V | 62.6 | 0.5 | 6.0 |
| 49 | Z | 59.8 | 1 | 16 |
| 50 | AA | 69.5 | 0.4 | 15.8 |
| 51 | BB | 21.5 | 0.7 | 7.8 |
| 52 | CC | 63.4 | 1.4 | 15.1 |
| 53 | DD | 70.3 | 3.6 | 16.7 |

Catalyst Test Method A

Catalyst solutions were prepared by mixing 0.042 mmol of one of the bidentate ligands of the invention and 0.014 mmol of Ni(COD)$_2$ in 457 mg toluene.

Hydrocyanation of 3,4 Pentenenitrile (3,4 PN): 125 μL of a solution containing HCN, t-3PN, and 2-ethoxyethyl ether (0.396 mmol HCN, 0.99 mmol t-3PN) were added to a septum capped vial. 13 μL of a solution of ZnCl$_2$ in t-3PN (0.0067 mmol ZnCl$_2$) were added to the vial and the vial cooled to −20° C. After cooling, 116 μL (0.003 mmol Ni) of a catalyst solution prepared as described above were added to the vial. The vial was sealed and set aside for 24 hours at room temperature. After 24 hrs the reaction mixture was diluted with ethylether and the product distribution analyzed by GC using 2-ethoxyethyl ether as an internal standard. Reported yields are based on HCN consumed.

Catalyst Test Method B

A glass reactor fitted with a nitrogen bubbler was charged with 3-pentenenitrile (5 mL; 52 mmol), Ligand (0.42 mmol), Ni(COD)$_2$ (0.040 g; 0.14 mmol) and ZnCl$_2$ (0.020 g, 0.15 mmol) under inert nitrogen atmosphere. The mixture was heated to 50° C. and agitated with a magnetic stirrer. HCN was delivered to the reactor by sparging a source of liquid HCN (cooled to 0° C.) with dry nitrogen (30 cc/min) and directing the resulting saturated HCN/N$_2$ mixture into the reactor below the liquid level. Progress of the reaction is monitored by removing aliquots and analyzing by GC. After 1 hr the reaction is terminated.

| Example | ligand | conv | dist | method |
|---|---|---|---|---|
| 54 | EE | 8.8 | 95.5 | A |
| 55 | W | 72.2 | 97.5 | A |
| 56 | FF | 21.5 | 96.5 | A |
| 57 | B | 89.5 | 93.3 | A |
| 58 | X | 29.5 | 91.7 | A |
| 59 | Y | 26.0 | 71.0 | A |
| 60 | GG | 63.9 | 95.1 | B |
| 61 | CC | 42.2 | 92.6 | A |
| 62 | J | 13.0 | 88.6 | A |
| 63 | BB | 21.5 | 86.6 | A |

-continued

| Example | ligand | conv | dist | method |
|---------|--------|------|------|--------|
| 64 | H | 5.9 | 95.4 | B |
| 66 | DD | 64.5 | 91.2 | A |
| 67 | V | 13.0 | 83.0 | A |

What is claimed is:

1. A hydrocyanation process, comprising reacting an acyclic, aliphatic, monoethylenically unsaturated compound in which the ethylenic double bond is not conjugated to any other olefinic group in the molecule with a source of HCN in the presence of a catalyst precursor composition comprising a Lewis acid, a zero-valent nickel, and a multidentate phosphite ligand selected from the group represented by the formulae I, I-A or I-B:

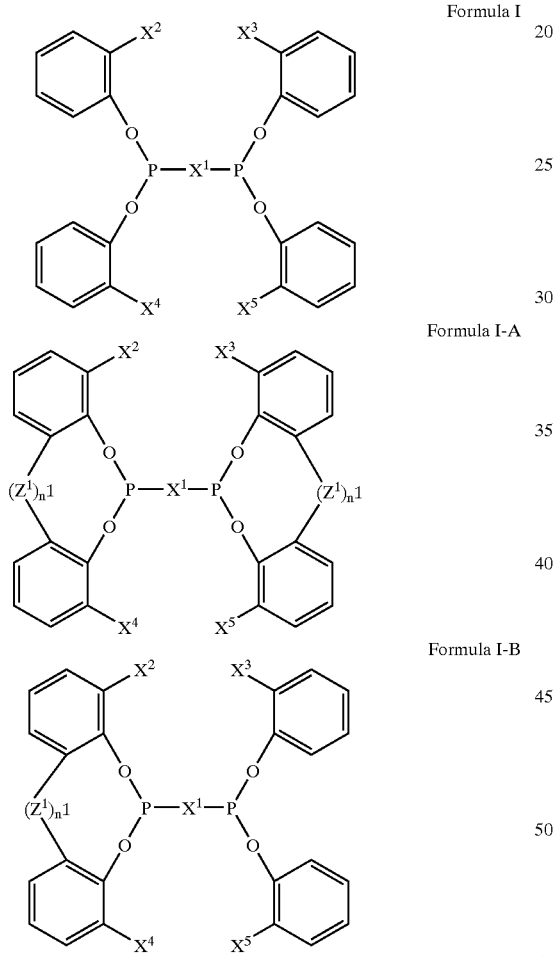

Formula I

Formula I-A

Formula I-B wherein $X^1$ is a bridging group selected from the group consisting of

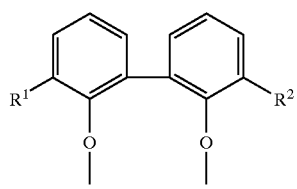

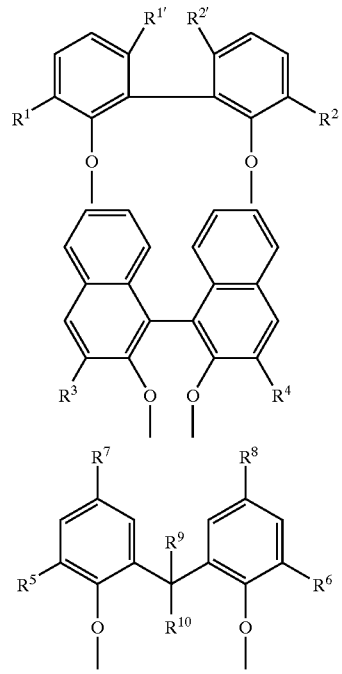

wherein $R^1$, $R^2$, $R^3$, $R^4$, $R^5$, $R^6$, $R^7$, $R^8$, $R^{1'}$, and $R^{2'}$ are independently selected from the group consisting of H, $C_1$ to $C_{18}$ alkyl, cycloalkyl, trialkylsilyl, triarylsilyl, halogen, nitrile, perfluoroalkyl, —$SO_2R^{11}$, —$SO_2NR_2^{12}$, acetal, ketal, dialkylamino, or diarylamino, —$OR^{11}$, —$CO_2R^{11}$, —$(CNR^{11})R^{11}$, —$(CNOR^{11})R^{11}$, wherein $R^{11}$ is $C_1$ to $C_{18}$ alkyl, cycloalkyl, aryl, or substituted aryl, —$C(O)R^{12}$, —$C(O)NR^{12}R^{13}$, —O—$C(O)R^{12}$, —$NR^{12}$—$C(O)R^{13}$, wherein $R^{12}$ and $R^{13}$ are independently selected from the group consisting of H, $C_1$ to $C_{18}$ allyl, cycloalkyl, aryl, or substituted aryl; wherein positions other than $R^1$ through $R^8$ on the aromatic rings may also be substituted with $C_1$ to $C_{18}$ alkyl, cycloalkyl, trialkylsilyl, triarylsilyl, halogen, nitrile, perfluoroalkyl, sulfonyl, acetal, ketal, dialkylamino, diarylamino, —$OR^{11}$, —$CO_2R^{11}$,R $CNR^{11}$, or $RCNOR^{11}$, wherein $R^9$ and $R^{10}$ are independently selected from the group consisting of H, $C_1$ to $C_{18}$ alkyl, cycloalkyl, aryl, or substituted aryl;

wherein $X^2$ through $X^5$ are independently selected from the group consisting of:

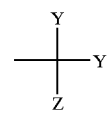

wherein Y is independently selected from the group consisting of H, aryl, $CR^{14}_3$, $(CR^{14}_2)n$—$OR^{14}$, $(CR^{14}_2)n$—$NHR^{15}$ wherein n=0–3; wherein $R^{14}$ is H, $C_1$–$C_{18}$ alkyl, cycloalkyl, or aryl; wherein $R^{15}$ is selected from the group consisting of H, alkyl, cycloalkyl, aryl, —$SO_2R^{11}$, —$SO_2NR^{12}_2$, —$COR^{16}$; and wherein $R^{16}$ is H, $C_1$–$C_{18}$ alkyl; aryl, or perfluoroalkyl;

wherein Z is selected from the group consisting of $(CR^{14}_2)_n$—$OR^{14}$ wherein n=0–3 and wherein $R^{14}$ is defined as above; and wherein, optionally, either one of the Y's may be linked with Z to form a cyclic ether;

wherein a ligand of the structure of Formula I-A or Formula I-B has at least one aromatic ring carbon in the ortho position to an O bonded to a P bonded through $(Z^1)n^1$ to another aromatic ring carbon in the ortho position to the other O bonded to the P;

wherein $Z^1$ is independently; and

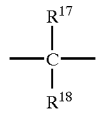

wherein each $R^{17}$ and $R^{18}$ are independently selected from the group consisting of H, $C_1$ to $C_{18}$ alkyl, cycloalkyl aryl, or substituted aryl, and $n^1$ is either one or zero.

2. The process of claim 1 wherein the ligand has the structure of formula I.

3. The process of claim 1 wherein, in at least one of the groups $X^2$–$X^5$, a Y is linked with Z to give the structure of formulae A or B; and wherein $Y^3$=O or $CH_2$; and $R^{14}$ is defined as above:

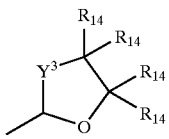

Formula A

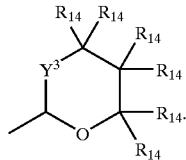

Formula B

4. The process of claim 1 wherein the Lewis acid is selected from the group consisting of inorganic or organometallic compounds in which one element of said compound is selected from scandium, titanium, vanadium, chromium, manganese, iron, cobalt, copper, zinc, boron, aluminum, yttrium, zirconium, niobium, molybdenum, cadmium, rhenium and tin.

5. The process of claim 4 wherein the Lewis acid is selected from the group consisting of $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2(tetrahydrofuran)_2$, $TiCl_4(tetrahydrofuran)_2$, $TiCl_4$, $TiCl_3$, $ClTi(OiPr)_3$, $MnCl_2$, $ScCl_3$, $AlCl_3$, $(C_8H_{17})AlCl_2$, $(C_8H_{17})_2AlCl$, $(iso$-$C_4H_9)_2AlCl$, $(phenyl)_2AlCl$, phenyl$AlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $TaCl_5$, $CdCl_2$, $B(C_6H_5)_3$, and $(C_6H_5)_3SnX$, wherein X=$CF_3SO_3$, $CH_3C_6H_5SO_3$, or $(C_6H_5)_3BCN$.

6. The process of claim 1 wherein the ethylenically unsaturated compound is selected from the group consisting of 3-pentenenitrile, 4-pentenenitrile; alkyl 2-, 3-, and 4-pentenoates, and $C_zF_{2z+1}CH$=$CH_2$, wherein z is an integer of 1 to 12.

7. The process of claim 6 wherein the ethylenically unsaturated compound is 3-pentenenitrile or 4-pentenenitrile.

8. The process of claim 1 which is carried out at a temperature of −25° C. to 200° C. and at a pressure of 50.6 to 1013 kPa.

9. The process of claim 8 which is carried out at atmospheric pressure and at a temperature of 0° C. to 150° C.

* * * * *